United States Patent
Evans et al.

(10) Patent No.: US 10,182,732 B2
(45) Date of Patent: *Jan. 22, 2019

(54) ECG SYSTEM WITH MULTI MODE ELECTRODE UNITS

(71) Applicant: EasyG LLC, Beverly Hills, MI (US)

(72) Inventors: Thomas Crannell Evans, Beverly Hills, MI (US); Efraim Gavrilovich, Vancouver (CA); Rasvan Catalin Mihai, Vancouver (CA); Ion Isbasescu, Burnaby (CA)

(73) Assignee: EasyG LLC, Milwaukee, WI (US)

( * ) Notice: Subject to any disclaimer, the term of this patent is extended or adjusted under 35 U.S.C. 154(b) by 1080 days.

This patent is subject to a terminal disclaimer.

(21) Appl. No.: 14/377,255

(22) PCT Filed: Feb. 8, 2013

(86) PCT No.: PCT/US2013/025432
§ 371 (c)(1),
(2) Date: Aug. 7, 2014

(87) PCT Pub. No.: WO2013/120014
PCT Pub. Date: Aug. 15, 2013

(65) Prior Publication Data
US 2015/0005609 A1  Jan. 1, 2015

Related U.S. Application Data

(60) Provisional application No. 61/596,543, filed on Feb. 8, 2012.

(51) Int. Cl.
*A61B 5/00* (2006.01)
*A61B 5/0408* (2006.01)
(Continued)

(52) U.S. Cl.
CPC ........ *A61B 5/04085* (2013.01); *A61B 5/0006* (2013.01); *A61B 5/0205* (2013.01);
(Continued)

(58) Field of Classification Search
CPC .............. A61B 5/04011; A61B 5/7214; A61B 5/04021; A61B 5/0002; A61B 5/0006;
(Continued)

(56) References Cited

U.S. PATENT DOCUMENTS 3,938,507 A * 2/1976 Sarnoff ................ A61B 5/0006
128/901
4,558,309 A * 12/1985 Antonevich ......... G01R 31/026
340/649

(Continued)

FOREIGN PATENT DOCUMENTS

WO    2010131267    11/2010

OTHER PUBLICATIONS

Gilboy et al., "Noninvasive Monitoring of End-Tidal Carbon Dioxide in the Emergency Department", Advanced Emergency Nursing Journal, vol. 28, No. 4, pp. 301-313, 2006.

*Primary Examiner* — Eunhwa Kim
(74) *Attorney, Agent, or Firm* — Chernoff, Vilhauer, McClung & Stenzel, LLP

(57) ABSTRACT

Systems and apparatus for monitoring heart muscle activity of an individual include a first electrode unit, for receiving a first signal indicative of electrical, activity at a first location on a body of the individual and a second electrode unit for receiving a second, signal indicative of electrical activity at a second location on the body of the individual. Each of the first and second electrode units is configurable to operate in a field-sensing mode wherein the electrode unit is placed on or it! proximity to the individual's skin, and a current-sensing mode wherein the electrode unit is coupled (Continued)

to a resistive sensor sensing element placed directly on the individual's skin. The field-sensing mode can be either non-contact field-sensing mode.

48 Claims, 8 Drawing Sheets

(51) Int. Cl.
    *A61B 5/044*     (2006.01)
    *A61B 5/0205*     (2006.01)
    *A61B 5/0416*     (2006.01)
    *A61B 5/0452*     (2006.01)
    *A61B 5/05*     (2006.01)

(52) U.S. Cl.
    CPC ............ *A61B 5/044* (2013.01); *A61B 5/0408* (2013.01); *A61B 5/0416* (2013.01); *A61B 5/6844* (2013.01); *A61B 5/7214* (2013.01); *A61B 5/0452* (2013.01); *A61B 5/05* (2013.01); *A61B 2562/0214* (2013.01)

(58) Field of Classification Search
    CPC .................. A61B 5/18; A61B 5/6893; A61B 2562/021464
    See application file for complete search history.

(56) References Cited

U.S. PATENT DOCUMENTS

| | | | |
|---|---|---|---|
| 4,781,197 A | 11/1988 | Fukuda | |
| 4,890,630 A * | 1/1990 | Kroll | A61B 5/04085 128/902 |
| 5,195,523 A * | 3/1993 | Cartmell | A61B 5/0416 600/391 |
| 5,466,256 A * | 11/1995 | McAdams | A61N 1/046 600/391 |
| 6,611,705 B2 | 8/2003 | Hopman et al. | |
| 6,728,576 B2 | 4/2004 | Thompson et al. | |
| 6,807,438 B1 | 10/2004 | Brun Del Re et al. | |
| 6,897,788 B2 | 5/2005 | Khair et al. | |
| 6,961,601 B2 * | 11/2005 | Matthews | A61B 5/0408 600/372 |
| 6,987,965 B2 | 1/2006 | Ng et al. | |
| 7,171,166 B2 | 1/2007 | Ng et al. | |
| 7,173,437 B2 | 2/2007 | Hervieux et al. | |
| 7,197,357 B2 | 3/2007 | Istvan et al. | |
| 7,885,700 B2 | 2/2011 | Clark et al. | |
| 7,996,056 B2 | 8/2011 | Rowlandson et al. | |
| 8,188,862 B1 | 5/2012 | Tam et al. | |
| 8,274,386 B1 | 9/2012 | Dea et al. | |
| 8,502,666 B1 | 8/2013 | Tam et al. | |
| 2002/0044059 A1 * | 4/2002 | Reeder | A61B 5/0002 340/573.1 |
| 2002/0072682 A1 | 6/2002 | Hopman et al. | |
| 2003/0036691 A1 | 2/2003 | Stanaland et al. | |
| 2003/0040305 A1 * | 2/2003 | Ng | A61B 5/0006 455/419 |
| 2003/0083735 A1 * | 5/2003 | Denardo | A61B 17/12118 623/1.15 |
| 2004/0068195 A1 | 4/2004 | Massicotte et al. | |
| 2004/0073104 A1 | 4/2004 | Brun del Re et al. | |
| 2004/0251057 A1 * | 12/2004 | Suzuki | A61B 5/0537 177/25.13 |
| 2005/0154324 A1 * | 7/2005 | Lin | A61B 5/0404 600/509 |
| 2006/0058017 A1 | 3/2006 | Ng et al. | |
| 2006/0089558 A1 | 4/2006 | Welles, II et al. | |
| 2007/0055166 A1 | 3/2007 | Patil | |
| 2007/0293774 A1 | 12/2007 | Acquista | |
| 2009/0018457 A1 * | 1/2009 | Hung | A61B 5/02438 600/509 |
| 2009/0054737 A1 | 2/2009 | Magar et al. | |
| 2009/0099469 A1 | 4/2009 | Flores | |
| 2009/0138059 A1 | 5/2009 | Ouwerkerk | |
| 2010/0049006 A1 | 2/2010 | Magar et al. | |
| 2011/0043225 A1 | 2/2011 | Sullivan et al. | |
| 2011/0208259 A1 | 8/2011 | Pearce et al. | |
| 2011/0270064 A1 | 11/2011 | Rowlandson et al. | |
| 2013/0150741 A1 | 6/2013 | Noh et al. | |

\* cited by examiner

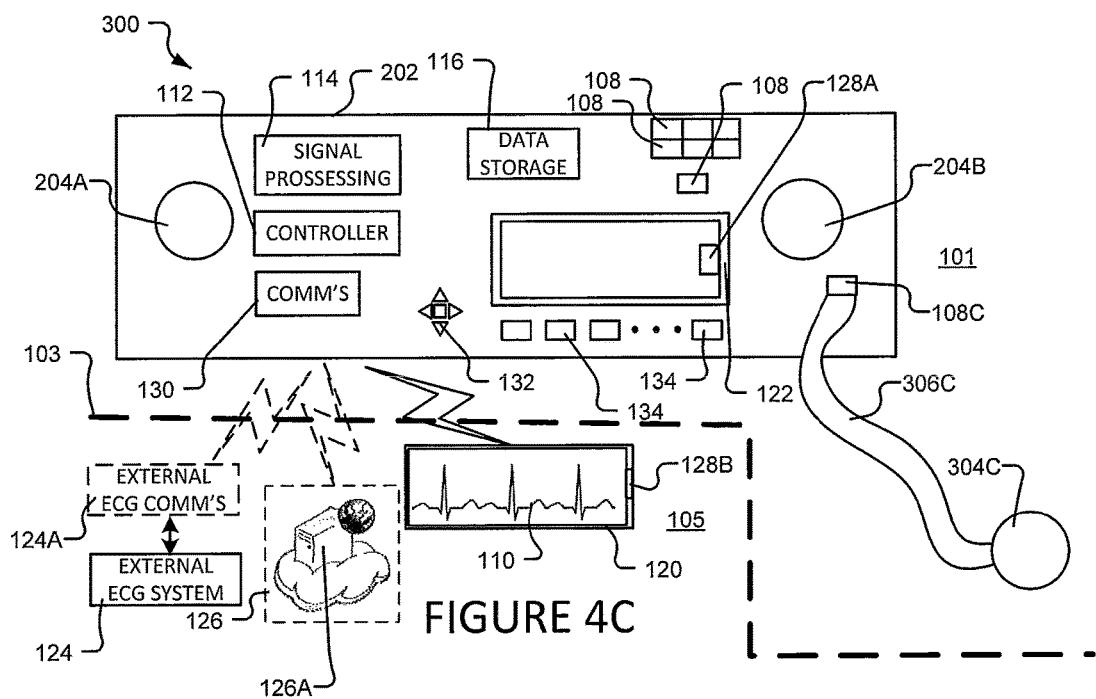

1

ECG SYSTEM WITH MULTI MODE ELECTRODE UNITS

CROSS-REFERENCE TO RELATED APPLICATION

This application claims priority from U.S. provisional application No. 61/596,543 filed Feb. 8, 2012 entitled REMOTE MONITORING ECG SYSTEM. This application claims the benefit under 35 U.S.C. § 119 of U.S. provisional application No. 61/596,543 filed Feb. 8, 2012 entitled REMOTE MONITORING ECG SYSTEM which is hereby incorporated herein by reference.

TECHNICAL FIELD

The technology described herein relates to electrocardiography (ECG) systems which detect electrical activity at locations on a patient's body.

BACKGROUND

A conventional ECG system typically consists of between 3 and 10 electrodes placed on areas of a patient's body to detect electrical activity. The electrodes are connected to an ECG monitor by a commensurate number of wires/cables. A conventional ECG electrode typically comprises a resistive sensor element which is placed directly against the patient's skin. A number of electrodes are placed against the patient's skin to detect the electrical characteristics of the heart (e.g. the current through or voltage across the resistive sensor element) at desired vantage points on the patient's body. The detected signals are relayed through the wires to the ECG monitor, which is typically located on a lab table or the like, away from the patient's body. A signal processing unit within the ECG monitor processes the signals to generate an ECG waveform which can be displayed on a display of the ECG monitor.

FIGS. 1 and 2 show three electrodes 10, 12, 14 arranged in the so-called Einthoven's triangle on a patient's body 16. As is known in the art, electrodes 10, 12 and 14 may be respectively referred to as the Right Arm (RA), Left Arm (LA) and Left Leg (LL) electrodes because of the locations that they are commonly placed on body 16. To generate an ECG signal, various potential differences are determined between the signals from electrodes 10, 12, 14. These potential differences are referred to as "leads". Leads have polarity and associated directionality. The common leads associated with the Einthoven's triangle shown in FIGS. 1 and 2 include: lead I (where the signal from RA electrode 10 is subtracted from the signal from LA electrode 12); lead II (where the signal from RA electrode 10 is subtracted from the signal from LL electrode 14); and lead III (where the signal from LA electrode 12 is subtracted from the signal from LL electrode 14). In addition to the leads shown in FIG. 2, other common leads associated with the Einthoven's triangle configuration include: the AVR lead (where one half of the sum of the signals from LA and LL electrodes 12, 14 is subtracted from the signal for RA electrode 10); the AVL lead (where one half of the sum of the signals from RA and LL electrodes 10, 14 is subtracted from the signal for LA electrode 12); and the AVF lead (where one half of the sum of the signals from RA and LA electrodes 10, 12 is subtracted from the signal for LL electrode 14). As is known in the art, the AVR lead is oriented generally orthogonally to lead III, the AVL lead is oriented generally orthogonally to lead II and the AVF lead is oriented generally orthogonally to lead I. The signals from each of these leads can be used to produce an ECG waveform 18 as shown in FIG. 3. Additional sensors can be added to provide different leads which may be used to obtain different views of the heart activity. For example, as is well known in the art, sensors for precordial leads V1, V2, V3, V4, V5, V6 may be added and such precordial leads may be determined to obtain the so-called 12lead ECG.

Some issues with traditional ECG technology make it an impediment for use, particularly in emergency response situations. The multiple electrodes and their corresponding wires may require extensive time to set up which may be critical in emergency circumstances. Having to maneuver around and detangle a large number of wires can be a nuisance. Multiple electrodes and wires can make it difficult to move a patient or administer medical aid to a patient. Signal noise from movement of the wires and wire tension can also degrade the quality of the ECG reading. Multiple wires can be particularly problematic during cardiac monitoring, where the ECG wires are attached to a patient for a long time. These issues with traditional ECG technology are exacerbated where there is a significant distance between the patient and the ECG monitor (i.e. where the electrode wires are long).

In addition to the problems with wires, current ECG systems use contact electrodes with resistive sensor elements. Such contact electrodes must be placed in direct contact with the patient's skin to obtain accurate signals. Typically, these contact electrodes are stuck to the patient's skin using an adhesive. The use of contact electrodes can be problematic in some circumstances. By way of non-limiting example, it may be undesirable or difficult to remove the patient's clothing in certain situations—e.g. where the patient may have privacy concerns, where the patient is suspected of having a spinal cord injury and/or the like. As another example, the patient may have a condition which makes it undesirable or difficult to apply current-sensing electrodes to the skin—e.g. the patient is suffering from burns to their skin, the patient has body hair which must be removed prior to using the contact electrodes, the patient is allergic to the adhesive and/or the like.

There is a general desire for improved ECG systems. By way of non-limiting example, there is a general desire for an ECG system that can provide greater flexibility for use by medical professionals in a variety of different circumstances, such as might be the case for emergency response technicians (EMTs). There is a general desire for ECG systems that may be more convenient and/or simple to use than existing ECG systems.

The foregoing examples of the related art and limitations related thereto are intended to be illustrative and not exclusive. Other limitations of the related art will become apparent to those of skill in the art upon a reading of the specification and a study of the drawings.

SUMMARY

One aspect of the invention provides a system for monitoring heart muscle activity of an individual comprising: a first electrode unit for generating a first signal indicative of electrical activity of the heart muscle at a first location on a body of the individual; and a second electrode unit for generating a second signal indicative of electrical activity of the heart muscle at a second location on the body of the individual. Each of the first and second electrode units is configurable to operate in: a field-sensing mode wherein the electrode unit is configured to generate its corresponding signal based on a detected electric field at a location on or in proximity to the individual's skin; and a current-sensing mode wherein the electrode unit is configured to generate its corresponding signal based on current flow through a resistive sensor element placed directly on the individual's skin.

Another aspect of the invention provides an electrode unit for use in an ECG system comprising: a capacitive sensor element for detecting electric field; a spring-biased clamp for attachment of the electrode unit to an individual's clothing when operating in a non-contact field-sensing mode; and an attachment means for physical and electrical attachment of the electrode unit to a resistive sensor element when operating in a resistive mode.

Another aspect of the invention provides a system for monitoring heart muscle activity of an individual comprising: a first electrode unit for generating a first signal indicative of electrical activity of the heart muscle at a first location on a body of the individual, the first electrode unit comprising a first capacitive sensing element for detecting electric field; a second electrode unit for generating a second signal indicative of electrical activity of the heart muscle at a second location on the body of the individual, the second electrode unit comprising a second capacitive sensing element for detecting electric field; and a plurality of inputs, each input adapted to receive a corresponding signal from a current-sensing electrode unit indicative of electrical activity at a corresponding location on the body of the individual.

Another aspect of the invention provides a system for monitoring heart muscle activity of an individual comprising: a first input for receiving a first signal indicative of electrical activity of the heart muscle at a first location on a body of the individual; a second input for receiving a second signal indicative of electrical activity of the heart muscle at a second location on the body of the individual; wherein each of the inputs is adapted to receive a signal from a field-sensing electrode unit or from a current-sensing electrode unit and the system is configured to differentiate between signals received from field-sensing electrode units and signals received from current-sensing electrode units and to generate one or more ECG waveforms based on the received signals.

Another aspect of the invention provides a system for monitoring heart muscle activity of an individual comprising: a first field-sensing electrode unit for generating a first signal indicative of electrical activity of the heart muscle at a first location on a body of the individual, the first field-sensing electrode unit configured to generate the first signal based on a detected electric field at a location on or in proximity to the individual's skin; and a second current-sensing electrode unit for generating a second signal indicative of electrical activity of the heart muscle at a second location on the body of the individual, the second current-sensing electrode unit configured to generate the second signal based on current flow through a resistive sensor element placed directly on the individual's skin; wherein the system is configured to combine the first signal and the second signal to generate an ECG waveform.

Another aspect of the invention provides a method for generating a ECG waveform related to heart muscle activity of an individual, the method comprising: providing a plurality of electrode units, each electrode unit configured to generate a corresponding signal indicative of electrical activity of the heart muscle at a corresponding location on a body of the individual; operating at least one first one of the plurality of electrode units in a field-sensing mode, wherein the at least one first one of the electrode units is configured to generate its corresponding signal based on a detected electric field at a location on or in proximity to the individual's skin; operating at least one other one of the plurality of electrode units in a current-sensing mode, wherein the at least one other one of the plurality of electrode units is configured to generate its corresponding signal based on current flow through a resistive sensor element placed directly on the individual's skin; and using the signals generated by the at least one first one of the plurality of electrode units and generated by the at least one other one of the plurality of electrode units to generate one or more ECG waveforms.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced figures of the drawings. It is intended that the embodiments and figures disclosed herein are to be considered illustrative rather than restrictive.

FIG. 4C schematically illustrates an ECG system architecture according to another particular embodiment.

DESCRIPTION

Throughout the following description, specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
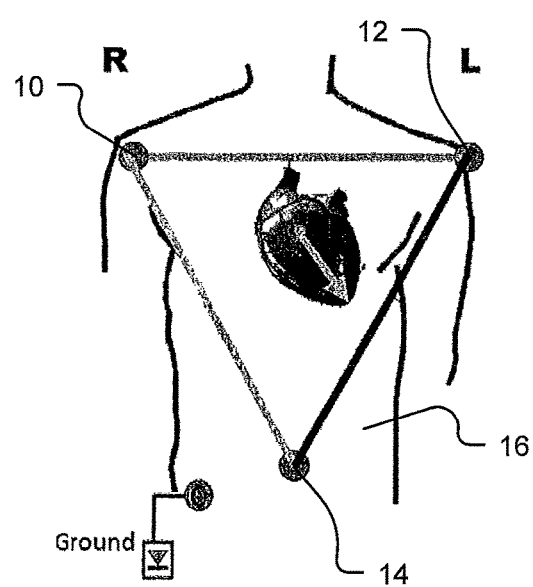
FIG. 1 is a schematic illustration of the electrodes of a conventional ECG system arranged on the patient's body in an Einthoven's triangle configuration.
Figure 2:
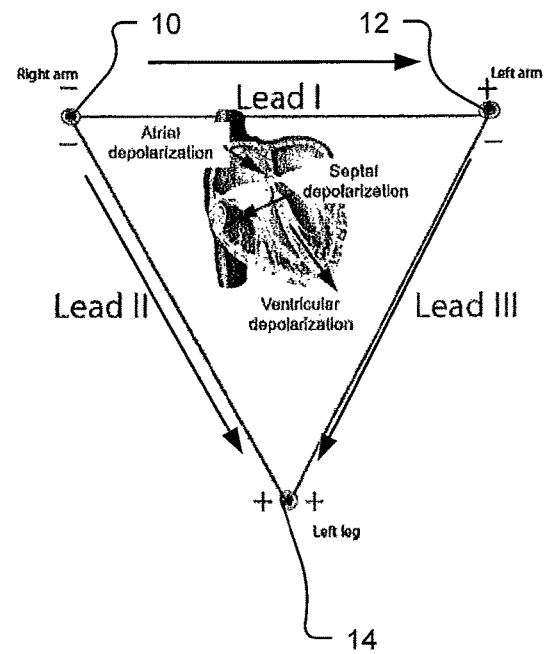
FIG. 2 is a schematic illustration of the electrodes of a conventional ECG system arranged in an Einthoven's triangle configuration and a number of the corresponding leads.
Figure 3:
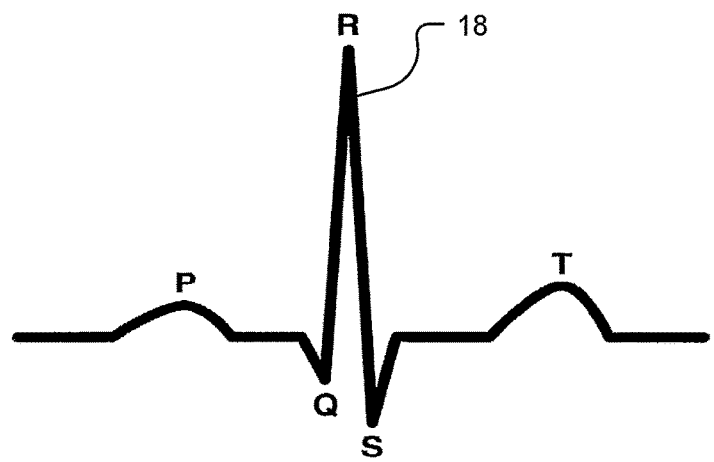
FIG. 3 is a typical ECG waveform of the type that might be displayed on an ECG system.
Figure 4A:
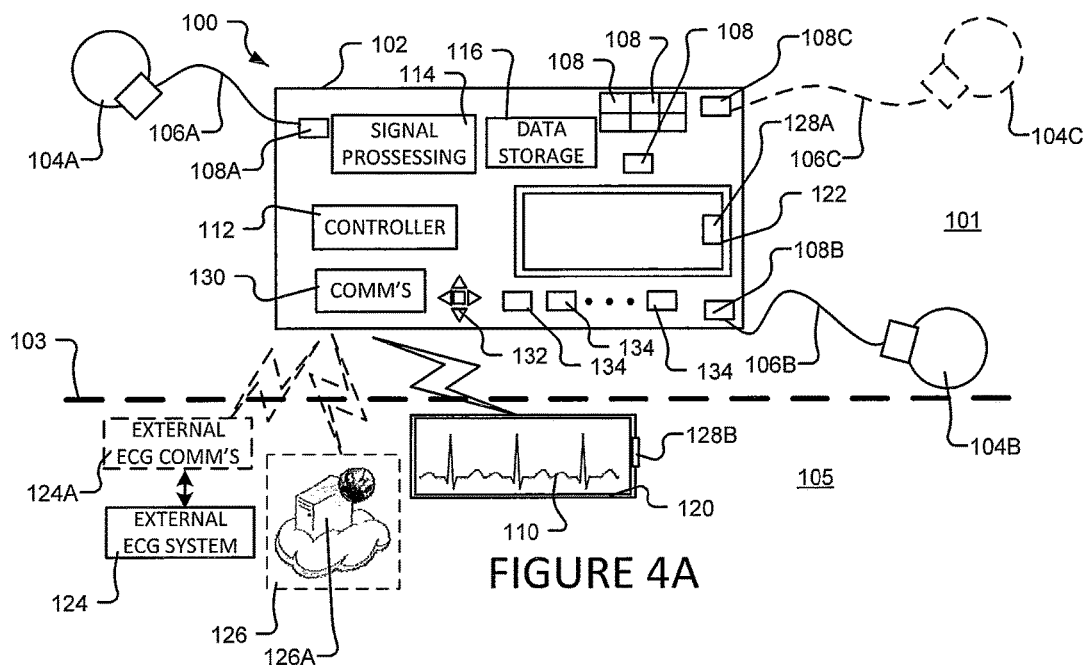
FIG. 4A schematically illustrates an ECG system architecture according to a particular embodiment.

FIG. 4A schematically illustrates an ECG system 100 according to a particular embodiment. ECG system 100 comprises a base unit 102 and two or more electrode units 104A, 104B, 104C (collectively and individually, electrode units 104). Electrode units 104 may be located relative to a patient's body 101 (as discussed in more detail below) to generate signals indicative of electrical activity of the patient's heart at their corresponding locations. In the schematic illustration of FIG. 4A, locations 101 on the patient's body are shown as being above the thick dashed line 103 and locations 105 away from the patient's body are shown as being below the thick dashed line 103. In currently preferred embodiments, electrode units 104 are multi-function electrode units of the type described below, although this is not necessary. In the illustrated embodiment of FIG. 4A, ECG system 100 is shown as having three electrode units 104A, 104B, 104C which may be used in an Einthoven's triangle configuration. In some embodiments, third electrode unit 104C is not necessary and system 100 may use as few as two electrode units 104. In some embodiments, system 100 may be provided with more than three electrode units 104 (as discussed in more detail below) to provide additional leads and corresponding additional views of heart muscle electrical activity.

In the FIG. 4A embodiment, electrode units 104 are removably connected to base unit 102 by corresponding cables 106A, 106B, 106C (collectively and individually, cables 106) which may be removably connected to base unit 102 using suitable electrical, signal transmission connectors 108A, 108B, 108C (collectively and individually, connectors 108). Connectors 108 may comprise, for example: slidable locking electric connectors, spring-biased electric connectors, magnetic connectors and/or the like. Base unit 102 is preferably constructed to be sufficiently small and lightweight that it can comfortably rest on a patient's body 101 without discomfort and without impacting the patient's ECG waveform. By way of non-limiting example, base unit 102 could be rested on a patient's chest, strapped or clipped (using suitable straps (not shown) or clips (not shown)) to the patient's clothing, arm or leg, and/or the like. With base unit 102 being so proximate to the patient, cables 106 may be correspondingly short. In some embodiments, cables 106 are less than 50 cm in length. In some embodiments, cables 106 are less than 30 cm in length.

In the illustrated embodiment, ECG waveforms 110 generated by ECG system 100 are displayed on a display 120. In some embodiments, display 120 may be integral with base unit 102. However, in the illustrated embodiment, display 120 is removably attached to base unit 102 at cradle 122, so that display 120 can be separated from base unit 120 to a location 105 away from the patient's body to permit easy reading by medical professionals without requiring the medical professionals to lean over top of or otherwise crowd the patient's body 101. In the illustrated embodiment, ECG waveforms 110 are wirelessly communicated to display 120 when display 120 is detached from base unit 102. When display 120 is located in cradle 122, ECG waveforms 110 may be provided directly (via a suitable complementary connectors 128A, 128B) to display 120—i.e. without wireless communication.

Base unit 102 may comprise suitably configured hardware and/or software components for processing signals from electrode units 104 and for generating corresponding ECG waveform(s) 110 for display on display 120. In the illustrated embodiment, such components include: a controller 112, signal processing hardware 114, data storage 116, communications hardware 130 and user interface components 132. For simplicity, only a number of components germane to the present invention are described in detail here. It will be appreciated by those skilled in the art that base unit 102 may comprise other electronic components suitable for operation as described herein. These components may be configured to provide particular functionality using suitably coded software (not explicitly shown). Controller 112 may interact with and control the other functional components of ECG system 100. By way of non-limiting example, controller 112 may comprise any suitable controller, such as, for example, a suitably configured computer, microprocessor, microcontroller, field-programmable gate array (FPGA), other type of programmable logic device, pluralities of the foregoing, combinations of the foregoing, and/or the like. Controller 112 may have access to software which may be stored in computer-readable memory (not shown) accessible to controller 112 and/or in computer-readable memory that is integral to controller 112. Controller 112 may be configured to read and execute such software instructions and, when executed by controller 112, such software may cause controller 112 to implement one or more of the methods described herein.

Signal processing hardware 114 may comprise any suitable analog or digital signal conditioning and/or signal processing components for generating ECG waveforms 110 from the signals obtained from electrode units 104. By way of non-limiting example, signal processing hardware 114 may comprise amplifiers, buffers, filters, analog to digital converters, suitably configured digital signal processors and/or the like. Data storage 116 may comprise any suitable memory (e.g. solid state memory) that may be used to store digital ECG data. In some embodiments, data storage 116 may be integrated into other components (e.g. controller 112 or signal processing hardware 114). In some embodiments, data storage 116 is not necessary.

Communications hardware 130 may comprise suitable hardware (e.g. WAN interfaces, LAN interfaces) for wireless communication according to one or more wireless digital communications protocols. Non-limiting examples of such protocols, include: a suitable Bluetooth communication protocol; wireless USB protocol; 802.11 wireless protocol; Zigbee protocol and/or the like. In some embodiments, display 120 may not be detachable from base unit 102 in which case display 120 may be connected via suitable electrical contacts. In some embodiments, display 120 may be removable from cradle 122, but attached to base unit 102 with a signal communication cable or the like. In such embodiments, some or all of communications hardware 130 may not be required. In some embodiments, communications hardware 130 may facilitate communication of ECG data (e.g. data stored in data storage 116, real time ECG waveforms 110 and/or the like) from base unit 102 to an external ECG system 124. In some embodiments, where external ECG system 124 is not capable of wireless communications or of wireless digital communications, ECG system 100 may comprise a suitable external ECG system communications component 124A which may be used to communicate with communications hardware 130 and to convert any received data/signals from communications hardware into a format capable of being interpreted by external ECG system 124. External ECG system communications component 124A may comprise hardware similar to any of the hardware described herein for base unit 102.

In some embodiments, communications hardware 130 may facilitate communication of ECG data (e.g. data stored in data storage 116, real time ECG waveforms 110 and/or the like) from base unit 102 to another device 126A (e.g. a computer or the like) via a network 126 or via a direct communication link (not shown) for further processing and/or display. By way of non-limiting example, network 126 may comprise: a local area network (LAN), such as a hospital network, a work place network or the like; or a wide area network (WAN), such as the Internet, a cellular network or the like). In some embodiments, communications hardware 130 may additionally or alternatively facilitate wired communication with external ECG system 124 or with another device 126A (e.g. a computer or the like) via a network 126.

Display 120 together with user interface inputs 130 may be used (by controller 112) to implement a text-based or graphical user interface (UI). User interface inputs 130 may comprise any suitable pointing device, buttons, touch screen and/or the like through which a medical professional can interact with and control ECG system 100. By way of non-limiting example, a medical professional could control such a user interface to: freeze ECG waveform 110 on display 120; view historical waveforms 110 or pulses; switch between the waveforms 110 of different leads; toggle between views of single ECG waveforms 110 or multiple ECG waveforms 110; zoom in on ECG waveform 110 on display 120; measure characteristics (e.g. amplitude and/or frequency) of ECG waveform 110; communicate with other devices (e.g. external ECG system 124 and/or another device via network 126); print to suitably configured printer device; toggle a "grph-paper" background on display 120; identify abnormal ECG rhythms; display measurements associated with other diagnostic equipment (explained in more detail below) which may be connected to ECG system 100 (e.g. blood pressure, blood sugar, pulse oximetry ($SpO_2$), body temperature and/or the like); display alarms or alerts associated with abnormalities measured by such other diagnostic equipment; provide temporal information (e.g. clocks or stopwatches), alarms and/or alerts; and/or the like.

Base unit 102 may comprise a number of additional connectors 108 for optional connection to additional electrode units 104 (not shown). For example, in the illustrated embodiment, base unit comprises seven additional connectors 108 for connection to seven additional electrode units 104. With a total of ten electrode units 104, ECG system can be configured to provide the so-called "12 lead" ECG functionality.

Base unit 102 may also comprise suitable connections 134 for connecting to other medical equipment (not shown). Such connections 134 may be used to accept data from such equipment (e.g. from medical diagnostic equipment). By way of non-limiting example, such medical diagnostic equipment may comprise a blood pressure cuff, a glucometer, a pulse oximetry ($SpO_2$) monitor, and end-tidal carbon dioxide ($ETCO_2$) monitor, a thermometer and/or the like. Connections 134 may also be used for other medical equipment. In some embodiments, connections 134 may be used to connect to a pair of defibrillator pads or paddles which may be used to deliver defibrillation shock(s) (e.g. pacing defibrillation, cardio version defibrillation and/or automatic external defibrillation) to a patient. While not expressly shown, base unit 102 may comprise a separate rechargeable battery which may be used to deliver such defibrillation shock(s).

Figure 4B:
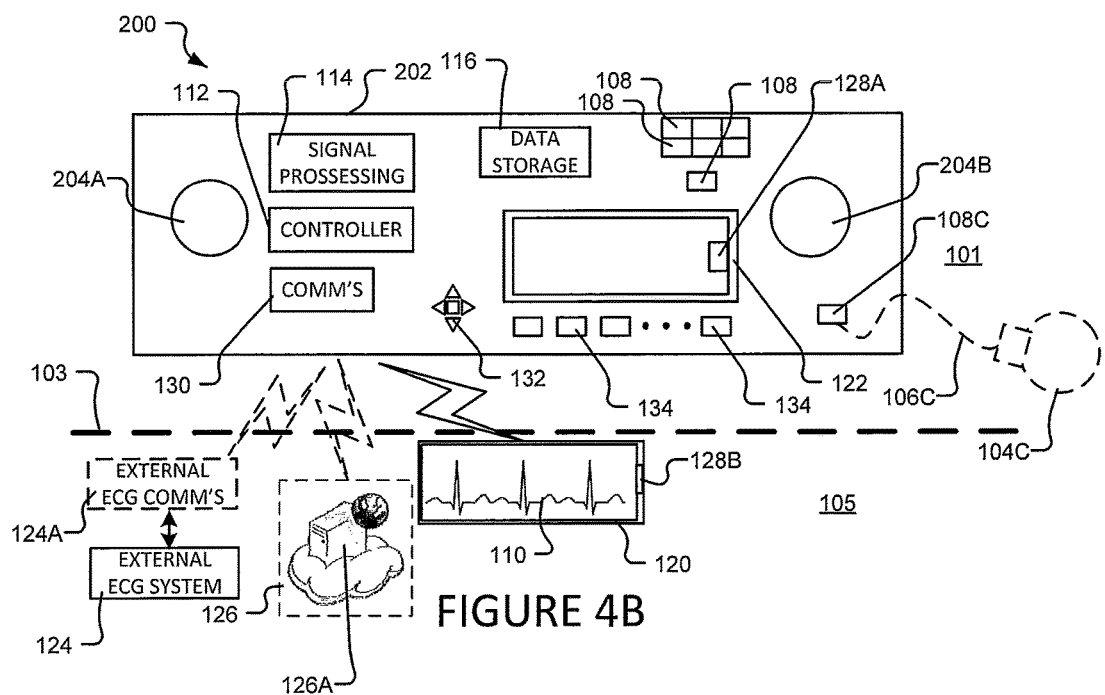
FIG. 4B schematically illustrates an ECG system architecture according to another particular embodiment.

FIG. 4B schematically illustrates an ECG system 200 according to a particular embodiment. ECG system 200 is similar in many respects to ECG system 100 described above and the same reference numerals are used to refer to features of ECG system 200 that are similar to features of ECG system 100. Like ECG system 100, ECG system 200 comprises a base unit 202 and two or more electrode units 204A, 204B (collectively and individually, electrode units 204). ECG system 200 differs from ECG system 100 principally in that electrode units 204 are integral with base unit 202. Other than being located within base unit 202, electrode units 204 may be substantially similar to electrode units 104 described herein.

In the illustrated embodiment, ECG system is shown as having a third electrode unit 104C which attaches to base unit 202 via cable 106C and connector 108C to facilitate operation of ECG system 200 in an Einthoven's triangle configuration. Third electrode unit 104C may be substantially similar to electrode units 104 described herein. In some embodiments, third electrode unit 104C is not necessary and system 100 may use as few as two electrode units 204. In some embodiments, a third electrode unit 204 may be provided as an integral part of base unit 202 (i.e. similar to electrode units 204 of the FIG. 4B embodiment). Like ECG system 100, ECG system 200 comprises connectors 108 for accepting additional electrode units 104 to provide additional leads and corresponding additional views of heart muscle electrical activity.

In some embodiments, electrode units 204 may be detachable from base unit 202—e.g. to sense electrical activity of the heart at different locations away from base unit 202. For example, electrode units 204 may be provided in suitable sockets (not expressly shown), so that they can function to sense heart activity within their corresponding sockets. But electrodes 204 may be removed from their sockets, so that they can be connected to base unit 202 by suitable cables and connectors (similar to cables 106 and connectors 108 described above for electrode units 104). In this manner, electrode units 204 may also be able to sense electrical activity at locations away from base unit 202.

In other respects, ECG system 200 may be substantially similar to ECG system 100 described herein.

FIG. 4C schematically illustrates an ECG system 300 according to a particular embodiment. ECG system 300 is similar in many respects to ECG systems 100, 200 described above and the same reference numerals are used to refer to features of ECG system 300 that are similar to features of ECG systems 100, 200. Like ECG system 200, ECG system 300 comprises a base unit 202 and two or more electrode units 204 that are integral with base unit 202. ECG system 300 differs from ECG systems 100, 200 described herein in that ECG system comprises a third electrode unit 304C which is connected to base unit 202 via connector 108C and extension arm 306C. Third electrode unit 304C may be substantially similar to electrode units 104 described herein and may permit ECG system 300 to operate in an Einthoven's triangle configuration. However, in ECG system 300 of the FIG. 4C embodiment, extension arm 306C is fabricated from flexible, semi-rigid (e.g. limited elasticity) material that may be deformed by the ECG operator and, once deformed, may retain its shape so that electrode unit 304C remains in a desired location relative to the patient's body 101 until extension arm 306C is intentionally reshaped or repositioned by the ECG operator. Suitable materials for extension arm 306C may include, for example, memory plastic and/or the like. In some embodiments, extension arm 306C may comprise a casing having the flexible, semi-rigid (e.g. limited elasticity) properties which may in turn house a cable (e.g. similar to cable 106 described herein). It will be appreciated that in some embodiments, any electrode units 104 described as being connected to their respective base units may be connected via flexible, semi-rigid (e.g. inelastic) extension arms similar to extension arm 306C.

In other respects, ECG system 300 may be substantially similar to ECG systems 100, 200 described herein.

Figure 4D:
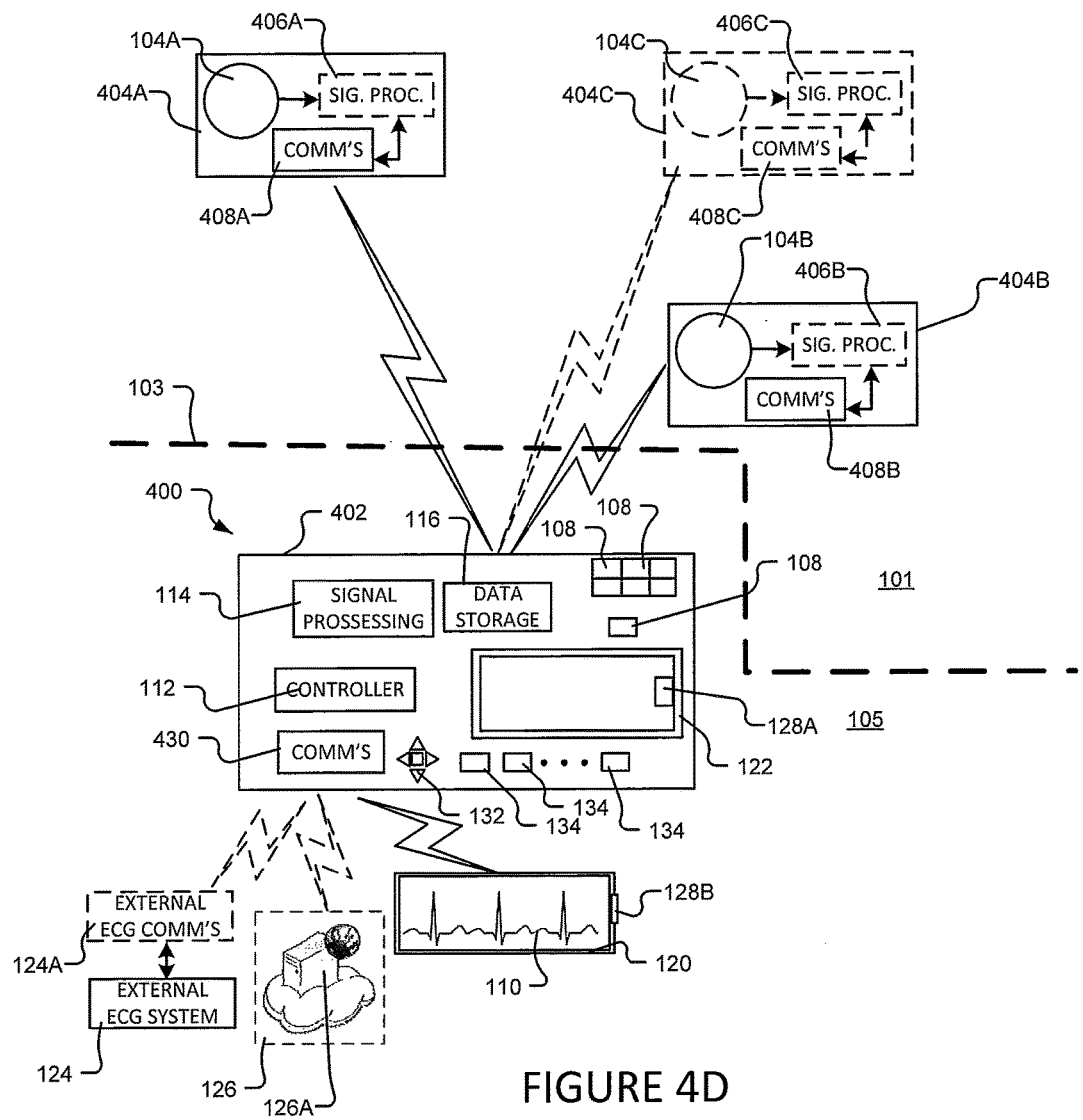
FIG. 4D schematically illustrates an ECG system architecture according to another particular embodiment.

FIG. 4D schematically illustrates an ECG system 400 according to a particular embodiment. ECG system 400 is similar in many respects to ECG systems 100, 200, 300 described above and the same reference numerals are used to refer to features of ECG system 400 that are similar to features of ECG systems 100, 200, 300. ECG system 400 comprises a base unit 402 and two or more electrode assemblies 404A, 404B, 404C (collectively and individually, electrode assemblies 404). Each electrode assembly 404A, 404B, 440C may comprise a corresponding electrode unit 104A, 104B, 104C which may be similar to electrode units 104 described herein. However, each electrode assembly 404A, 404B, 404C may comprise corresponding signal processing components 406A, 406B, 406C (collectively and individually, signal processing components) and communications components 408A, 408B, 408C (collectively and individually, communications components 408). Signal processing components 406 may comprise any suitable analog or digital signal components for conditioning and/or processing the signals obtained from electrode units 104. By way of non-limiting example, signal processing components 408 may comprise amplifiers, buffers, filters, analog to digital converters, suitably configured digital signal processors and/or the like. Communications components 408 may comprise any suitable hardware for analog or digital wireless communication of signals obtained from electrode units 104 (and processed by signal processing components 406) back to base unit 402. In this manner, base unit 402 may be positioned at a location 105 away from the patient's body 101. In some embodiments, electrode assemblies 404 may be electrically connected to one another (e.g. to provide a common ground or reference potential). In some embodiments, electrode assemblies 404 may share some of signal processing components 406 and/or communications components 408.

Electrode assemblies 404 may be located relative to a patient's body 101 (as discussed in more detail below) to generate signals indicative of electrical activity of the patient's heart at their corresponding locations and may wirelessly communicate these signals back to base unit 402 at a location 105 away from the patient's body 101. In the illustrated embodiment of FIG. 4D, ECG system 400 is shown as having three electrode assemblies 404A, 404B, 404C which may be used in an Einthoven's triangle configuration. In some embodiments, third electrode assembly 404C is not necessary and system 400 may use as few as two electrode assemblies 404. In some embodiments, system 400 may be provided with more than three electrode assemblies 404 to provide additional leads and corresponding additional views of heart muscle electrical activity. In some embodiments, electrode assemblies 404 may comprise suitably configured controllers (not shown) which may control signal processing components 406 and/or communications components 408.

Communications hardware 430 (and associated software) of ECG system 400 may differ from that of ECG systems 100, 200, 300 in that communications components 430 of ECG system 400 may be additionally configured to communicate wirelessly with electrode assemblies 404. In other respects, ECG system 400 may be substantially similar to ECG systems 100, 200, 300 described herein.

Figure 5A:
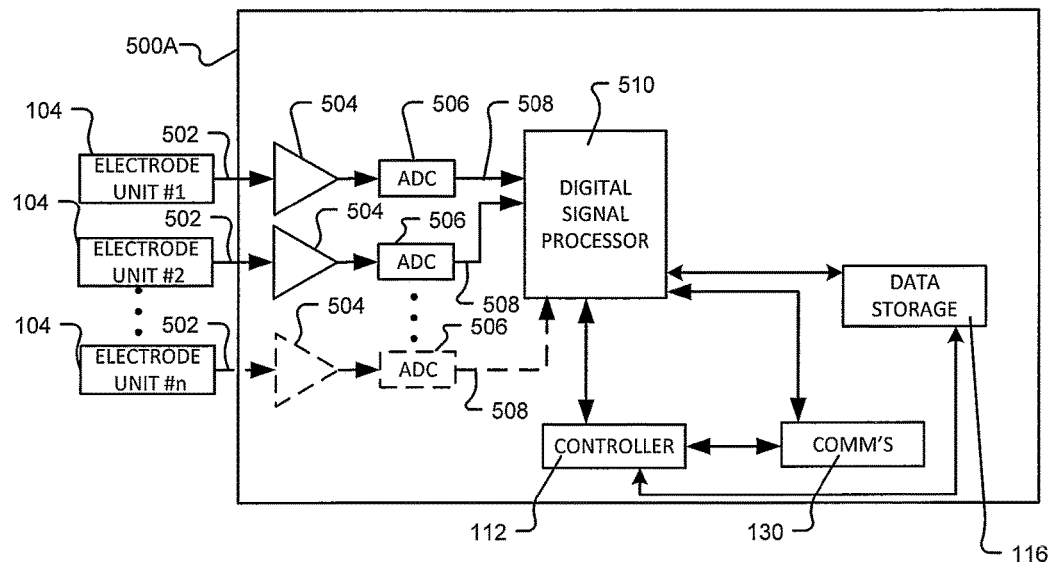
FIG. 5A is a block diagram showing one implementation of a signal processing system for processing data from the electrode units of the FIGS. 4A-4D ECG systems according to a particular embodiment.

FIG. 5A is a block diagram showing one implementation of a signal processing system 500A for processing data from electrode units 104 according to a particular embodiment. Signal processing system 500A may provide some of signal processing hardware 114 used with any of the ECG systems (e.g. ECG systems 100, 200, 300, 400) described herein. In some implementations, various portions of signal processing system 500A (e.g. amplifiers 504, ADCs 506 and or the like) could be implemented as parts of electrode units 104 (as opposed to being implemented as parts of base units 102, 202, 302, 402). In general, it will be appreciated that the components shown in the FIG. 5A schematic illustration are functional components which could be implemented by various forms of suitably configured hardware.

Signal processing system 500A receives analog data from electrode units 104. Each electrode unit 104 generates a corresponding analog signal 502 which is amplified by a corresponding amplifier 504 and digitized by a corresponding analog-to-digital converter (ADC) 506 before being provided (as a digital signal 508) to digital signal processor (DSP) 510. In some embodiments, DSP 510 may include integral ADC converters 506. DSP 510 may be configured to generate leads from digital signals 508 and to generate corresponding ECG data (e.g. ECG waveform 110). Digital signal processor 510 may additionally be configured to filter the various digital signals 508 (and/or combinations of such signals). For example, DSP 510 may be configured to filter various signals (or combinations of signals) to remove or mitigate the effects of breathing and/or other sources of artifacts. DSP 510 may addition or alternatively function to apply active noise cancellation algorithms, based on inverted ambient noise data. DSP 510 may additionally or alternatively scale signals 508 received from electrode units 104 operating in different modes (explained in more detail below). DSP 510 may additionally or alternatively provide synchronization functionality by introducing time delays to one or more of signals 508. Such time delays may be determined based on temporal correlation functions as between signals 508 and/or based on feature (e.g. edges, peaks and/or the like) detection within signals 508. DSP 510 also combines the various signals 508 to generate leads and corresponding ECG waveforms.

As is known in the art of digital signal processing, DSP 510 may be configured to process signals using functionality such as sample and hold functions, data acquisition functions, multi stage filtering and bandwidth limiting, filtering based for example on a rolling window, averaging functions, peak detection, temporal alignment of signals provided by different electrode units 104, positive and negative edge detection, time duration of PQRST portion of the ECG signal and relationship between them. Digital signal processor 510 may be controlled by controller 112. In some embodiments, however, DSP 510 and controller 112 may be implemented by the same hardware. In the FIG. 5A embodiment, DSP 510 has access to data storage 116. In some embodiments, all or part of data storage 116 may be integral to DSP 510. DSP 510 may output ECG data to data storage 116 and/or to display 120 (via communications components 130) and may provide the background functionality for such outputs. As discussed above, in some embodiments when display 120 is located in cradle 122 or when display is integral with base unit 102, ECG data may be provided directly to display 120 without involving communications hardware 130.

Figure 5B:
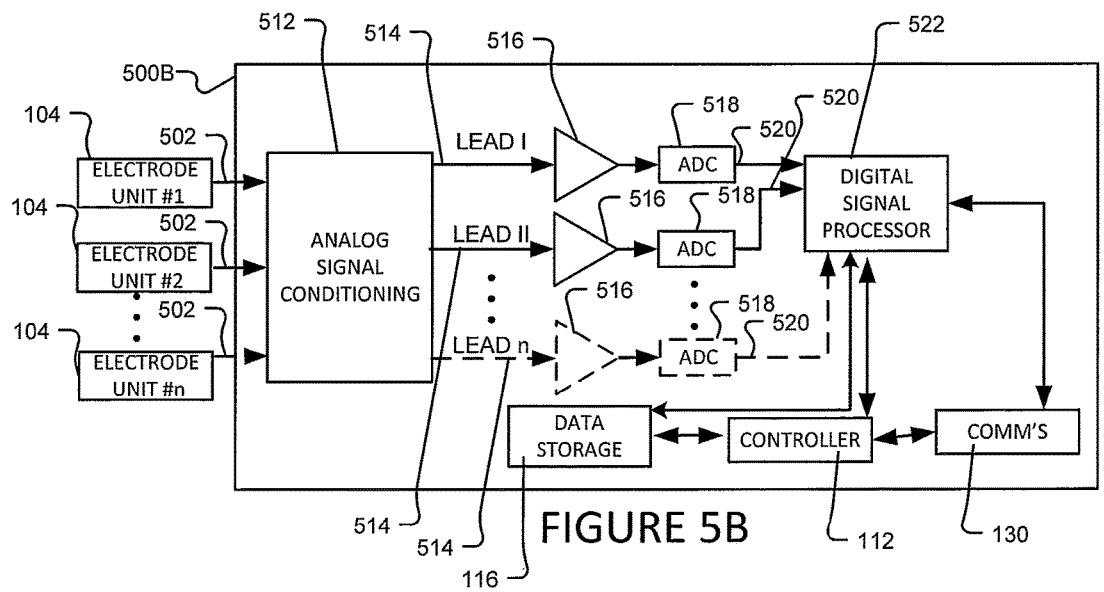
FIG. 5B is a block diagram showing one implementation of a signal processing system for processing data from the electrode units of the FIGS. 4A-4D ECG systems according to another particular embodiment.

FIG. 5B is a block diagram showing one implementation of a signal processing system 500B for processing data from electrode units 104 according to another particular embodiment. Signal processing system 500B may provide some of signal processing hardware 114 used with any of the ECG systems (e.g. ECG systems 100, 200, 300, 400) described herein. Signal processing system 500B receives analog data from electrode units 104. Each electrode unit 104 generates a corresponding analog signal 502 which is received at analog signal conditioning block 512. Analog signal conditioning block 512 comprises various amplifiers (e.g. summing amplifiers and/or differential amplifiers and/or inverting amplifiers) which combine analog signals 502 in various ways known in the art to generate leads 514. Each lead 514 is then amplified by a corresponding amplifier 516 and digitized by a corresponding analog-to-digital converter (ADC) 518 before being provided (as a digital lead signal 520) to digital signal processor (DSP) 522. Digital signal processor 522 may then be configured to use digital lead signals 520 to generate corresponding ECG data (e.g. ECG waveform 110). Other than for receiving leads (as opposed to signals from electrode units 104), DSP 522 may comprise and provide functionality similar to that described above for DSP 510.

A description of electrode units is now provided. For the sake of brevity, the description of electrode units refers to electrode units 104, it being understood that electrode units 204, 304 may have similar features. In some embodiments, one or more of electrode units 104 comprise resistive sensor elements for sensing the current through or voltage across the resistive sensor element. Electrode units 104 which comprise resistive sensor elements may be referred to herein as current-sensing electrode units (without loss of generality that the voltage across resistive sensor elements could be detected). Current sensing electrode units 104 operate by placing the resistive sensor element in direct contact with a patient's skin. In some embodiments, one or more of electrode units 104 comprise capacitive sensor elements which detect the presence of electric field. Electrode units 104 which comprise capacitive sensor elements may be referred to herein as field-sensing electrode units. Unlike resistive sensor elements, the capacitive sensor elements of field-sensing electrode units 104 do not require direct contact with the skin and may function by being placed close to the patient's body (e.g. overtop of clothes).

ECG systems 100, 200, 300, 400 described may use either (or both) of current-sensing electrode units 104 and field-sensing electrode units 104. Each of connectors 108 may be capable of accepting either current-sensing electrode units 104 or field-sensing electrode units 104. In particular embodiments, a combination of current-sensing electrode units 104 and field-sensing electrode units 104 may be used in any of ECG systems 100, 200, 300, 400 to monitor the heart muscle electrical activity of the patient. The choice of which particular electrode unit 104 may depend on the preferences of the system's operator, the electrode units that are currently available, and the circumstances (e.g. whether it is difficult to remove the patient's clothing, or whether the patient already has exposed skin at the desired vantage points).

In particular embodiments, one or more of electrode units 104 that is used in systems 100, 200, 300, 400 may comprise a multi-mode electrode unit 104 which can be configured to operate in one of a plurality of different modes. Such multi-mode electrode units 104 may operate as current-sensing electrode units by providing a resistive sensor element placed in direct contact with a patient's skin (i.e. under the patient's clothing (or at least with no intervening clothing between the sensor and the patient's skin)). Such multi-mode electrode units 104 may also operate as field-sensing electrode units which involve placing a capacitive sensor element in direct contact with a patient's skin (i.e. under the patient's clothing (or at least with no intervening clothing between the sensor and the patient's skin)). When such field-sensing electrode units are placed in direct contact with a patient's skin (i.e. under the patient's clothing (or at least with no intervening clothing between the sensor and the patient's skin)), such electrode units may be referred to herein as operating in "contact" mode. Such multi-mode electrode units 104 may also operate as field-sensing electrode units which involve placing a capacitive sensor element on top of the patient's clothing and not directly against the skin. When the patient's clothing is located between the electrode unit and the patient's skin, the electrode unit may be referred to herein as operating in "non-contact" mode. Since current-sensing electrode units typically require direct contact with the skin (i.e. no intervening clothing) to detect a signal, it is not necessary to describe current-sensing electrode units as operating in contact mode or non-contact mode, it being understood that when a current-sensing electrode unit 104 is operative, it operates in contact mode.

Figure 6A:
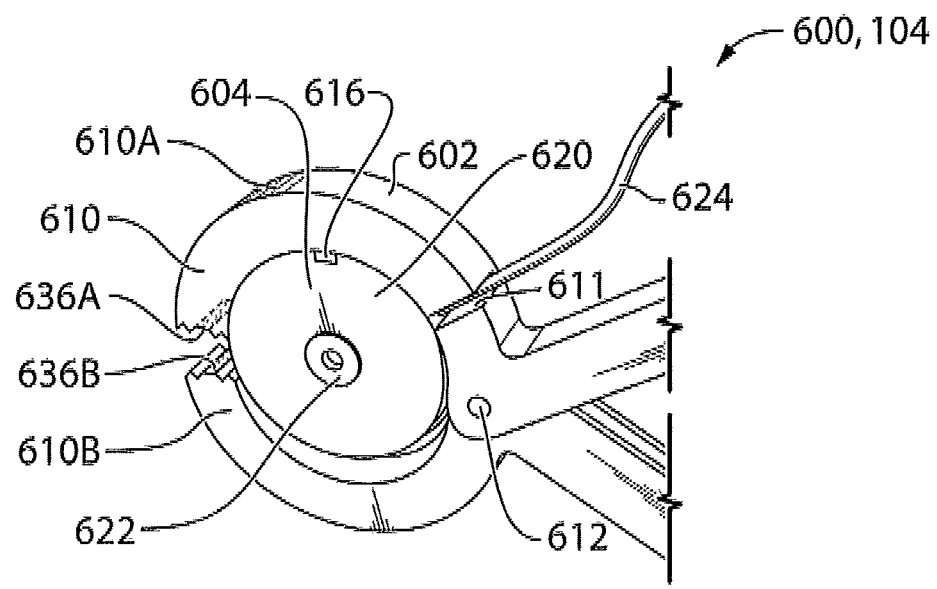
FIGS. 6A and 6B are respectively assembled and exploded isometric views of a multi-mode electrode unit according to a particular embodiment.
Figure 6B:
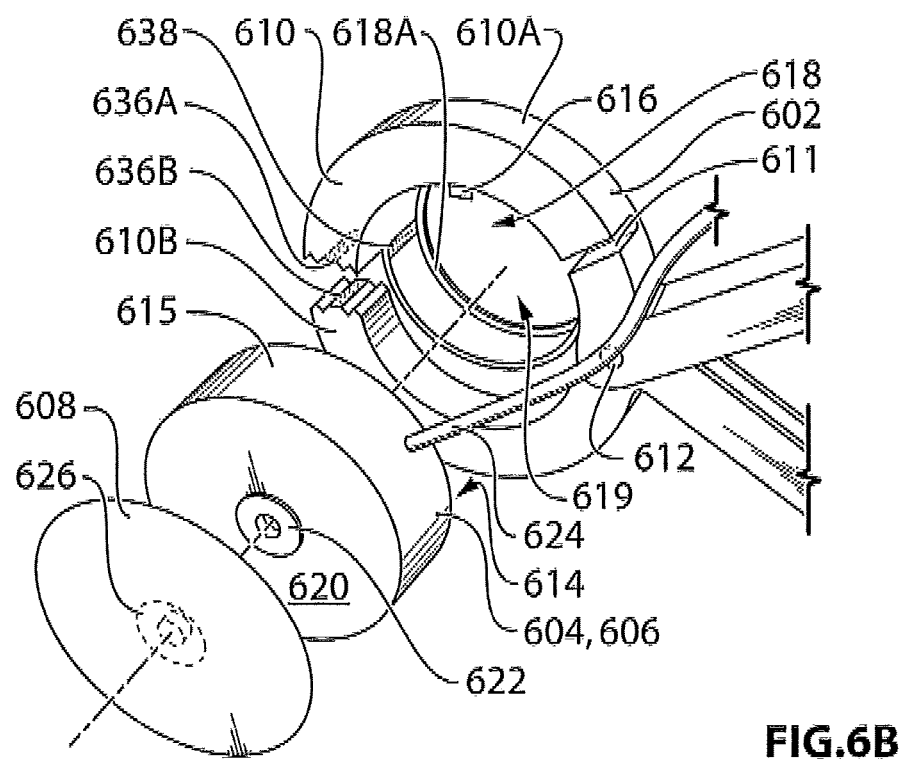

FIGS. 6A and 6B show a multi-mode electrode unit 600, which may be used for electrode unit 104 of any of ECG systems 100, 200, 300, 400. Multi-mode electrode unit 600 may be configured for operation in field-sensing contact mode, field-sensing non-contact mode and/or current-sensing mode. Any one or more of electrode units 104, 204, 304 may comprise an electrode unit 600 of the type shown in FIGS. 6A and 6B. Electrode unit 600 comprises a clamp portion 602 and a sensor portion 604 which is removably attached to clamp portion 602. As discussed in more detail below, sensor portion 604 comprises a capacitive sensor element 606 which permits electrode unit 600 to operate in a field-sensing contact mode (where sensor portion 604 is in direct contact with the patient's skin) or a field-sensing non-contact mode (where sensor portion 604 is located outside of the patient's clothing or otherwise is not in contact with the patient's skin). Further, at least one of clamp portion 602 and sensor portion 604 comprise a mechanism for electrical connection with a resistive sensor element 608 (FIG. 6B) which permits electrode unit 600 to operate in a current-sensing mode. Because electrode unit 600 can be placed either on skin or atop clothing and because electrode unit 600 can operate as a current-sensing electrode unit or a field-sensing electrode unit, electrode unit 600 is versatile and can be used in a range of different situations. For example, in some situations it may be desirable or more convenient to leave the clothing on the patient and to place the electrode unit 600 on top of the patient's clothing. In other situations the patient's skin may be exposed at desired vantage points—for example, the patient's torso may be exposed to allow the performance of a procedure (such as, by way of non-limiting example, defibrillation, CPR, insertion of a chest tube and/or the like) which requires direct contact with or exposure of the sking and so in those cases it may be convenient to place electrode unit 600 directly against the skin.

When electrode unit 600 operates in a field-sensing, non-contact mode, electrode unit 600 is placed over the patient's clothing. As seen in FIGS. 6A and 6B, electrode unit 600 comprises a clamp 610. In the illustrated embodiment of FIGS. 6A and 6B, clamp 610 comprises a pair of arms 610A, 610B which are pivotally connected to one another at pivot joint 612 and which are biased toward each other (e.g. by a suitably connected spring, a suitable deformable element and/or the like (not shown)) so that clamp 610 is biased toward a closed configuration. Arms 610A, 610B can be used to grip a part of the patient's clothing to attach the electrode unit 600 to the patient's clothing at the desired vantage point while the electrode unit 600 is being operated in field-sensing, non-contact mode. More particularly, when electrode unit 600 is operated in field-sensing, non-contact mode, a portion of the patient's clothing may be grasped between arms 601A, 601B of clamp 610 and proximate surface 614 of sensor portion 604 may be positioned directly atop the patient's clothing. This permits capacitive sensor element 606 to sense the electric field associated with the patient's heart-muscle activity and to provide a corresponding signal on one or more conductors of cable 624 which may be conveyed back to the base unit of the ECG system. Cable 624 may comprise one of cables 106 described above (see FIG. 4A, for example).

In some embodiments, sensor portion 604 is removably attached to clamp portion 602, so that sensor portion 604 may optionally be detached from clamp portion 602 (FIG. 6B) for use of sensor portion 604 in field-sensing, contact mode. More particularly, as can be seen by comparing FIGS. 6A and 6B, sensor portion 604 may be attached to clamp portion 602 (e.g. retained in cavity 618 in the particular case of the illustrated embodiment) to provide a unitary electrode unit 600 and sensor portion 604 may also be detached from clamp portion 602 to provide sensor portion 604 separately. When sensor portion 604 is separated from clamp portion 602, the proximate surface 614 of sensor portion 604 may be placed into contact with a patient's skin to permit capacitive sensor element 606 to sense the electric field associated with the patient's heart-muscle activity in a contact mode and to provide a corresponding signal on one or more of the conductors of cable 624 which is conveyed back to the base unit of the ECG system.

It is not necessary that sensor portion 604 be removed from clamp portion 602 for operation of electrode unit 600 in field-sensing, contact mode. In some embodiments, electrode unit 600 (including clamp portion 602 and sensor portion 604) may be located such that proximate surface 614 of sensor portion 604 is adjacent the patient's skin. For example, as shown in FIG. 6B, cavity 618 (in which sensor portion 604 is retained) comprises a rim 618A around its peripheral edge, but rim 618A defines an opening 619 which permits proximate surface 614 of sensor portion 604 to directly contact a patient's skin. With this configuration, capacitive sensor element 606 is able to sense the electric field associated with the patient's heart-muscle electrical activity in a field-sensing, contact mode (and to provide a corresponding signal to the ECG base unit on cable 624) even when sensor portion 604 is attached to clamp portion 602.

Sensor portion 604 and/or clamp portion 602 may comprise a locking mechanism 616 for keeping sensor portion 604 attached to clamp portion 602. In the FIG. 6A, 6B embodiment, sensor portion 604 is received in cavity 618 of clamp portion 602 and a spring-biased locking mechanism 616 extends (radially inwardly in the case of the illustrated embodiment) over an edge of distal surface 620 of sensor portion 604. When spring-biased locking mechanism 616 extends over the edge of distal surface 620 of sensor portion, locking mechanism 618 holds sensor portion 604 in cavity 618 (e.g. against rim 618A) and thereby locks sensor portion 604 into attachment with clamp portion 602. To detach sensor portion 604 from clamp portion 602, an operator may slide locking mechanism 616 against the spring bias (radially outwardly in the case of the illustrated embodiment) to remove sensor portion 604 from cavity 618. Some embodiments may comprise a plurality of spring-biased locking mechanisms 616. In some embodiments, sensor portion 604 may be locked to clamp portion 602 using different additional or alternative locking mechanisms. In the illustrated embodiment, when sensor portion 602 is located in cavity 618, cable 624 which is attached to sensor portion 604 runs through a channel 611 formed in a sidewall of cavity 618 of clamp portion 602. In other embodiments, cable 624 may run through different features when sensor portion 604 is attached to clamp portion 602.

In some embodiments, when electrode unit 600 is being used in field-sensing, contact mode, electrode unit 600 (or sensor portion 604 of electrode unit 600) may be adhered to the skin of the patient using adhesive tape, adhesive stickers, a suctioning mechanism or other means. For example, a double-sided adhesive sticker or tape can be placed between the patient's skin and electrode unit 600 (or sensor portion 604 of electrode unit 600) to adhesively connect electrode unit 600 (or sensor portion 604 of electrode unit 600) to the patient's skin. Similarly, adhesive tape can be applied over top of electrode unit 600 to tape electrode unit 600 in contact with a patient's skin and to permit electrode unit 600 to be used in field-sensing contact mode. In some embodiments, electrode unit 600 (or sensor portion 604 of electrode unit 600) may comprise a suction cup or suction hole (not shown) fluidly coupled to a suctioning bulb (not shown). The bulb may be squeezed prior to placement of the suction cup/hole on the patient's skin. Once the suction cup/hole is placed on the skin, the bulb is released to create a suctioning connection between the suction cup/hole and the skin, thereby holding electrode unit 600 (or sensor portion 604 of electrode unit 600) against the patient's skin. In some embodiment, a piece of tape may be applied to the patient's skin with an end portion of the tape extending away from the patient's skin. The end portion of the tape may then be adhered to a side surface 615 of sensor portion 604 or the end portion of the tape may be gripped between arms 610A, 610B of clamp 610 to help hold electrode unit 600 (or sensor portion 604 of electrode unit 600) against the patient's skin to thereby facilitate operation in field-sensing contact mode.

In addition to operating in field-sensing non-contact mode and field-sensing contact mode as discussed above, electrode unit 600 also operates in current-sensing mode. More particularly, at least one of clamp portion 602 and sensor portion 604 comprise a mechanism for electrical connection with a resistive sensor element 608 (FIG. 6B) which permits electrode unit 600 to operate in a current-sensing mode. In the illustrated embodiment, sensor portion 604 of electrode unit 600 comprises a snap-mechanism 622 for connection to a complementary snap-mechanism 626 on resistive sensor element 608. In the illustrated embodiment, snap-mechanism 622 is located on distal surface 620 of sensor portion 604. In other embodiments, snap mechanism 622 may be located on other surface(s) of sensor portion 604 and/or clamp portion 602. Snap mechanism 622 is in electrical contact with one or more conductors in cable 624 so that a signal may be conveyed back to the base unit of the ECG system via cable 624. The cable 624 conductor that is in electrical contact with snap mechanism 622 may be (but need not be) the same cable 624 conductor that is in electrical contact with the capacitive sensor element 606.

Figure 7A:
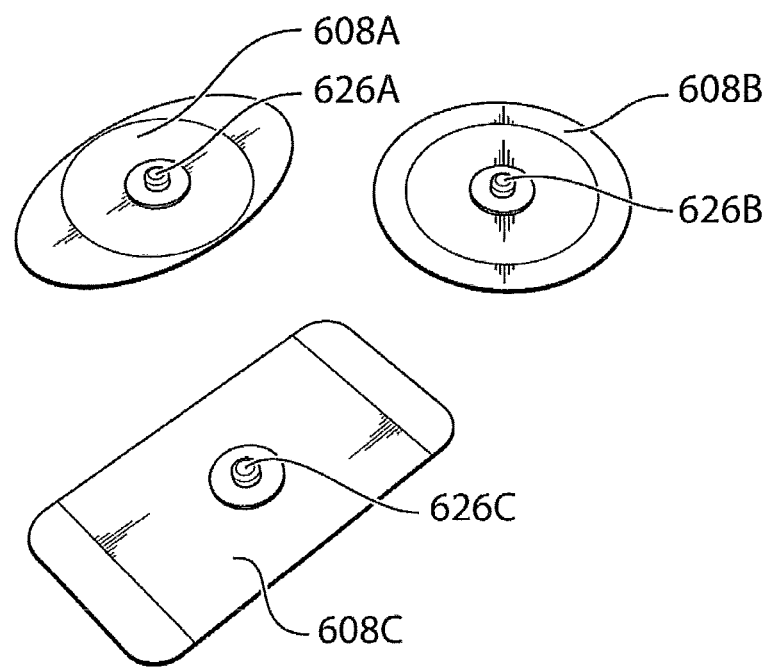
FIGS. 7A and 7B illustrate different resistive sensor elements that may be used with the FIGS. 6A, 6B electrode unit.

FIG. 7A shows a variety of resistive sensor elements 608A, 608B, 608C (collectively and individually, resistive sensor elements 608) of different shapes and sizes, each with a corresponding snap-mechanism 626A, 626B, 626C (collectively and individually, snap-mechanisms 626). In the current North American industry standard, snap-mechanisms 626 of resistive sensor elements are male snap-mechanisms 626. Accordingly, snap-mechanism 622 of electrode unit 600 may comprise a female snap-mechanism sized and shaped to mate with male snap-mechanisms 626 of resistive sensor elements 608. Snap-mechanisms 622, 626 are complimentary to one another, so that when they are engaged, there is a small amount of deformation of one or both of snap-mechanisms 622, 626 such that restorative forces associated with that deformation tend to lock snap-mechanisms 622, 626 to one another.

In use, a resistive sensor element 608 is connected to electrode unit 600 via a connection of snap-mechanisms 622, 626 and then the side of resistive sensor element 608 opposite snap-mechanism 626 is adhered to the skin of the patient for operative in current-sensing contact mode. Typically, resistive sensor elements 608 comprise an adhesive "peel and stick" type backing which may be used for this purpose. The heart muscle electrical activity signal detected by resistive sensor element 608 is conveyed via the contact between snap-mechanism 622, 626 to cable 624 and to the base unit of the ECG system. When operating in current-sensing mode, sensor portion 604 of electrode unit 600 may be removed from clamp portion 602 of electrode unit 600 is the same manner discussed above. This is not necessary, however, and electrode unit 600 may operate in current-sensing mode with sensor portion 604 connected to clamp portion 602.

Figure 7B:
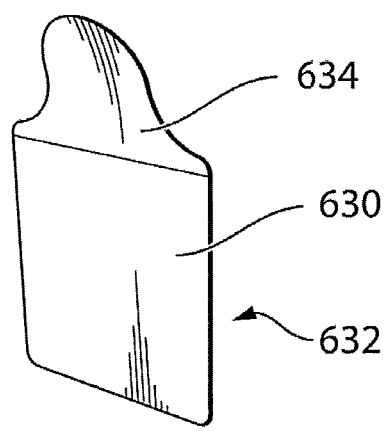

Resistive sensor elements 608 having snap-mechanisms 626 are common, but are not the only type of resistive sensor element. FIG. 7B depicts another type of resistive sensor element 630 which comprises an active surface 632 which may be adhered to the patient's skin (e.g. with a peel and stick type adhesive or a suitable external adhesive). Resistive sensor element 603 also comprises a tab 634, such that when active surface 632 is adhered to the patient's skin, tab 634 may be bent (or may otherwise extend) away from the patient's body. Multimode electrode unit 600 may also function in a current-sensing contact mode with resistive sensor elements 630. More particularly, tab 634 of resistive sensor element may be clamped between the arms 610A, 610B of clamp 610. One or both of the engagement surfaces of clamp 610 may be provided with electrical contacts 636A, 636B (collectively and individually, clamp contacts 636). Clamp contacts 636 may be electrically connected to transmit a current-sensing contact signal through electrode unit 600 and a conductor of cable 624 back to the base unit of the ECG system.

In the case of the illustrated embodiment, clamp contacts 636 are in electrical contact with electrical contact 638 (e.g. via a suitable wire or other conductor within one or both arms 610A, 610B of clamp 610. Electrical contact 638 may comprise any suitable electrical contact pin, plate, socket, shoe and/or the like. In the illustrated embodiment, electrical contact 638 is located on a wall of cavity 618. Sensor portion 604 may be provided with a complementary electrical contact (not shown in the illustrated view) which is in electrical contact with one of the conductors of cable 624. The electrical contact in sensor portion 604 may be complementary to electrical contact 638 and may comprise any suitable electrical contact pin, plate, socket, shoe and/or the like. In some embodiments, one or both of contact 638 and the contact in sensor portion 604 may be spring-loaded. When sensor portion 604 is connected to clamp portion 602 (e.g. sensor portion 604 is located in cavity 618 as shown in FIG. 6A of the illustrated embodiment), the electrical contact shoe of sensor portion 604 makes electrical contact with electrical contact shoe 638 of clamp portion 602, thus completing an electrical contact from clamp contacts 636, through electrical contact shoe 638 of clamp portion 602 and the electrical contact shoe of sensor portion 604 to a conductor of cable 624 and back to the base unit of the ECG system. In this manner, electrode unit 600 may work in current-sensing contact mode with resistive sensor element 630 and may convey heart activity signals back to the base unit of the ECG system.

In electrode unit 600 of the FIG. 6A, 6B embodiment, clamp 610 serves two functions. As described above, clamp 610 can be used to attach to a current-sensing element 630 so that electrode unit 600 can be operated in a current-sensing mode. Alternately, clamp 610 can be used to attach electrode unit 600 to clothing when the electrode unit 600 is being operated in a field-sensing non-contact mode. In other embodiments a separate clamping structure may be provided for each of these functions.

In the illustrated embodiment of FIGS. 6A and 6B, sensor portion 604 is connected to clamp portion 602 at a location between arms 610A, 610B of clamp portion 602. This is not necessary. In some embodiments, sensor portion 604 may be connected to other locations on clamp portion 602. By way of non-limiting example, sensor portion 604 may be connected to an outside of one of arms 610A, 610B of clamp portion 602 or within one of arms 610A, 610B of clamp portion 602—i.e. such that sensor portion 604 is not located between arms 610A, 610B. In the illustrated embodiment, sensor element 602 is generally round in cross-section. In other embodiments, sensor element 602 may have a keyed-shape (i.e. a protrusion from one its sidewall 615 and a corresponding groove in the sidewall of cavity 618 or vice versa) or some other cross-sectional shape. This may help to ensure alignment between electrical contact shoe 638 and the complementary electrical contact shoe on sensor portion 604.

In the description of FIGS. 6A and 6B above, signals from resistive sensor elements 608, 630 and from capacitive sensor elements 606 are conveyed back to the base unit of the ECG system via cable 624. Cable 624 may comprise one of cables 106 described above. Cable 624 may be connected to the base unit using a corresponding connector 108 (see FIG. 4A, for example). Connectors 108 may comprise multi-conductor (e.g. multi-pin) connectors. Such conductors/pins may comprise, without limitation: a ground pin; one or more current-sensing signal pins (e.g. one pin connected to snap-mechanism 622, one pin connected clamp contacts 636 or one pin connected to both snap-mechanism 622 and clamp contacts 636); and one or more field-sensing signal pins (e.g. connected to field-sensing element 606). In some embodiments, signals from both field-sensing element 606, snap mechanism 622 and clamp contacts 636 may be connected to the same pin of connectors 108. Cable 624 and connectors 108 may comprise additional pins for conveying additional information from electrode unit 600. For example, cable 624 may comprise conductors and connectors 108 may comprise pins for signals from proximity sensor(s) which may assist with determining the operational mode electrode unit 600, as explained below. As discussed above in FIG. 4D, electrode unit 600 may be provided as part of an electrode assembly 404 where signals are wirelessly conveyed from electrode assemblies 404 to the base unit of the ECG system. In such embodiments, cable 624 may be considered to be a suitable electrical contact to signal processing components 406 of electrode assembly 404—see FIG. 4D.

Where electrode units 104 of ECG systems 100, 200, 300, 400 are provided by multi-mode electrode units 600, an ECG system 100, 200, 300, 400 may be operated with its electrode units 600 operating in different modes. By way of non-limiting example, electrode units 104A, 104B may operate in any desired combination or permutation of: field-sensing non-contact mode (i.e. over clothing), field-sensing contact mode (i.e. directly against the patient's skin) and current-sensing mode. Similarly, each of electrode unit 104C and any additional electrode units connected to connectors 108 may operate in any desired one of: field-sensing non-contact mode, field-sensing contact mode and current-sensing mode.

The operation of electrode units 104 in different operational modes within a particular ECG system 100, 200, 300, 400 may yield corresponding electrical signals 502 (see FIGS. 5A, 5B) having different amplitudes. For example, an electrode unit 104 operating in current-sensing mode typically provides a signal 502 which is several orders of magnitude larger than an electrode unit 104 operating in field-sensing mode. Similarly, an electrode unit 104 operating in a field-sensing contact mode may yield a slightly stronger (e.g. 10%-50% stronger) signal 502 than an electrode unit 104 operating in field-sensing non-contact mode. Signals 502 having different amplitudes can be scaled or the like (e.g. by signal processing hardware 114) to normalize the signals prior to determining ECG leads (or other combined or differential signals). Suitable scaling factors can be pre-determined parameters, user-configurable parameters, system-configurable parameters or determined on an ad hoc basis. In one non-limiting example, digital signal processor 510 (FIG. 5A) may be configured to determine the amplitude (e.g. the maximum and minimum level) of each signal from each electrode unit 104 and to use this information to scale the signals from the various electrodes to normalize the signals to have at least approximately the same amplitude. In another non-limiting example, an amplifier or automatic gain control circuit (AGC) in analog signal conditioning circuitry 512 (FIG. 5B) may scale signals from electrode units operating in different modes by suitable pre-determined factor(s) in effort to normalize the signals from electrode units operating in different modes. In some embodiments, scaling may be non-linear.

In some circumstances, it may be desirable to determine the operational modes of electrode units 104 so that appropriate adjustments can be made to their corresponding signals before generating ECG leads (or other combined or differential signals). For example, where one electrode unit 104 is being operated in a field-sensing mode and another electrode unit 104 is being operated in a current-sensing mode, it may be desirable to scale the signals to have the same order of magnitude.

As discussed above with reference to FIGS. 6A and 6B, in some embodiments, signals from different operational modes of electrode unit 600 can be conveyed on different conductors of cable 624 and conveyed to the base unit of an ECG system through a different pin of connector 108. In this manner, the ECG system may be able to tell the operational mode of each of its electrode units 104. In some embodiments, an operator may additionally or alternatively provide information to the ECG system (e.g. via user inputs 132) to allow the ECG system to determine which electrode unit 104 is operating in which operational mode. In some embodiments, the strength of the signal from each electrode unit 104 may additionally or alternatively be used by the ECG system to determine the operational mode of each electrode unit 104. For example, a signal having an amplitude above a certain threshold may be indicative of a current-sending mode of operation.

In some embodiments, one or more additional sensors (not expressly shown) can additionally or alternatively be incorporated into electrode units 104 to assist with determining the mode of operation. For example, one or more first proximity sensors can be located in electrode unit 104 to detect a presence of a resistive sensor element (e.g. a resistive sensor element 608 connected to snap-mechanism 622 or a resistive sensor element 630 clamped between arms 610A, 610B of clamp 610). If the one or more first proximity sensors detect a resistive sensor element, then ECG system may conclude that electrode unit 104 is operating in current-sensing mode. One or more second proximity sensors can be located in electrode unit 104 to detect the proximity of the patient's skin. If the one or more second proximity sensors detect that the patient's skin is within a certain threshold distance and the one or more first proximity sensors do not detect a resistive sensor element, then ECG system may conclude that electrode unit 104 is operating in field-sensing contact mode. On the other hand, if the one or more second proximity sensors detect that the patient's skin is outside of the threshold distance and the one or more first proximity sensors do not detect the resistive sensor element, then it may be assumed that the electrode unit 104 is operating in a field-sensing non-contact mode. In some embodiments, the one or more second proximity sensors may be configured to detect the presence of a clamp portion of the electrode unit (explained in more detail below) and may conclude that electrode unit 104 is operating in a field-sensing non-contact mode when the clamp portion is sufficiently proximate or a field-sensing contact mode when the clamp portion is sufficiently far away.

It will be appreciated that the use of proximity sensors represent just one sensor-based technique for determining the operational mode of an electrode unit 104. Sensors other than proximity sensors may additionally or alternatively be used to help with the determination of the operations mode of an electrode unit 104. For example, suitable electrical contact sensors (e.g. micro-switches) and/or the like could be used to detect the presence of resistive sensor elements and/or clothing. For example, suitable proximity sensor, micro-switches, electrical contact sensors or the like could be used to detect whether or not clamp 610 is closed and could thereby be used to determine if a resistive sensor element or clothing was being held in clamp 610.

Figure 8:
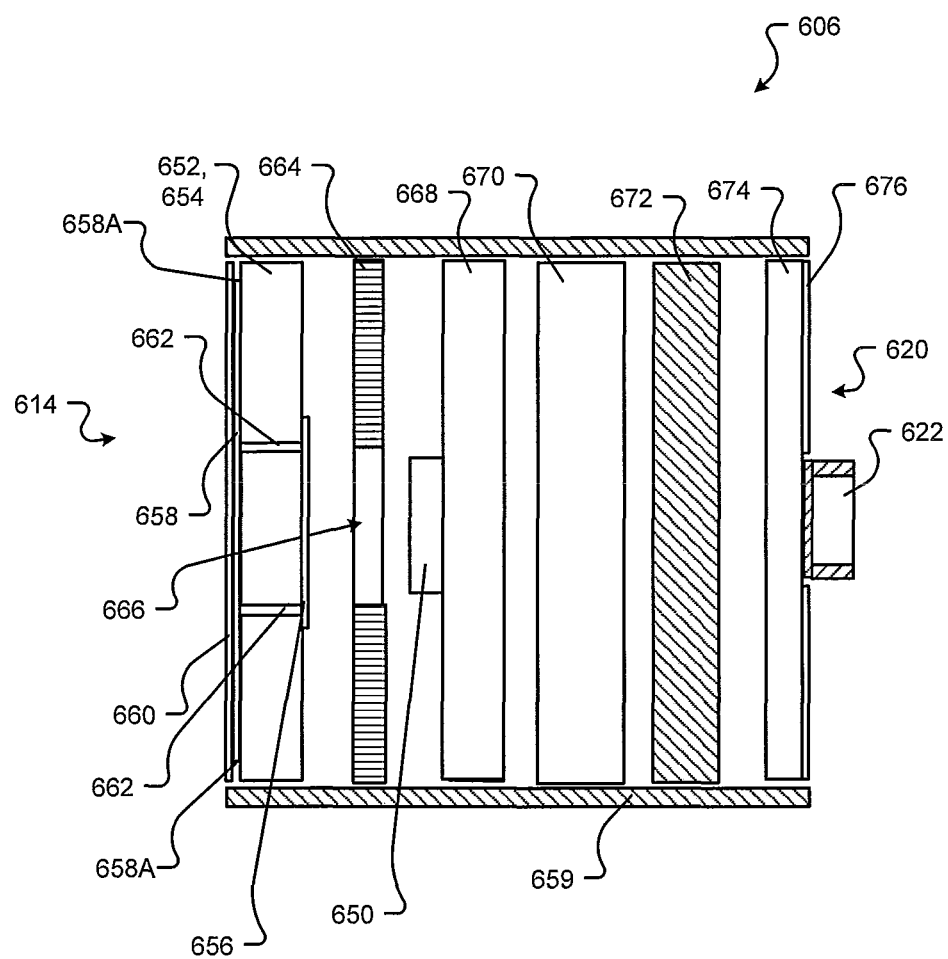
FIG. 8 is an exploded cross-sectional view of a capacitive sensor element that may be used with the FIG. 6A, 6B electrode unit according to a particular embodiment.

As discussed above, electrode unit 600 comprises a capacitive sensor element 606 which enables electrode unit 600 to operate in a field-sensing mode. FIG. 8 is an exploded cross-sectional view of a capacitive sensor element 606 that may be used with the FIG. 6A, 6B electrode unit 600 according to a particular embodiment. Capacitive sensor element 606 comprises proximate and distal surfaces 614, 620 corresponding to proximate and distal surfaces 614, 620 shown in FIG. 6B. The main sensor of capacitive sensor element 606 comprises an electrodynamic sensor 650 which is sensitive to local electric field. A non-limiting example of a suitable electrodynamic sensor 650 is described, for example, in U.S. Pat. No. 7,885,700. Another non-limiting example of a suitable electrodynamic sensor 650 is the sensor No. PS25205B marketed by Plessey Semiconductors Ltd. of the UK.

Capacitive sensor element 606 of the FIG. 8 embodiment comprises a number of components and layers:
  An antenna component 652 which serves as an antenna to increase electromagnetic signal sensitivity of electrodynamic sensor 650 and to improve the signal resolution of electrodynamic sensor 650. Antenna component 652 of the illustrated embodiment comprises a PCB core 654. On an inner side of PCB core 654, antenna component 652 comprise a layer of metallization (e.g. solder plated conductor) 656 which is in direct electrical contact with electrodymamic sensor 650 (described below). On an outer side of PCB core 654, antenna component 652 comprises a layer of metallization (e.g. solder plated conductor) 658, which is in turn coated with a thin non-conductive protective (e.g. solder mask) layer 660. Inner and outer metallization layers 656, 658 are electrically connected to one another by conductive vias 662 provided at suitable locations. Outer metallization layer 658 may be transversely recessed (e.g. by 1-5 mm) at its transverse edges 568A to insulate outer metallization layer 658 from sensor housing 659. Metallization layer 658 (and, possibly metallization layer 656) may serve as the radiating element of an antenna which is in electrical contact with the sensing surface of electrodynamic sensor 650. Metallization layer 658 and, possibly metallization layer 656 (i.e. the radiating element of antenna component 652) may have a surface area that is greater than a surface area of the sensing surface of electrodynamic sensor 650. In some embodiments, an outer peripheral rim of antenna component 652 could be provided with a stepped profile (e.g. an outer peripheral rim having less thickness in the left-to-right dimension of FIG. 8) to accommodate the thickness of rim 618A (see FIG. 6B).

A sensor-positioning layer 664 may be used on an inside of antenna layer 652 and may provide a cut-out 666 as shown to ensure the proper placement and/or orientation of electrodynamic sensor 650. Sensor-positioning layer 664 may comprise a suitable non-conductive PCB material or a single-layer PCB substrate with etched out copper layer.

A sensor-holding layer 668 which holds electrodynamic sensor 650. Sensor-holding layer 668 may comprise a sensor-holding PCB. Sensor-holding layer 668 may provide suitable solderable contacts to solder electrodynamic sensor 650 and suitable electrical connections to main PCB layer 672 described below. In some embodiments, sensor-holding layer 668 and main PCB layer 672 may comprise complementary (e.g. male and female) electrical contacts and/or connector components (not shown) that mate when sensor element 606 is assembled.

An insulator layer 670, which provides compressive force and facilitates proper electrical contact between the inner metallization layer 656 of antenna layer 652 and electrodynamic sensor 650. Insulation layer 670 may comprise Ethafoam™ material, for example. Insulator layer 670 may comprise a cut-out section (not shown) which permits electrical connections between sensor-holding layer 668 and main PCB layer 672 (as discussed above).

A main PCB layer 672 which houses the electronic circuitry (e.g. amplifiers, other signal conditioning components and/or the like) for operation of capacitive sensing element 606. Main PCB layer may provide electrical contact to cable 624 described with reference to FIGS. 6A and 6B above.

A distal component 674 serving as distal surface 620. Distal component 674 may comprise a metalized layer 676 which may provide electrical noise shielding. In the illustrated embodiment, metallization layer 676 is provided on the outside of distal component 674.

A snap-mechanism 622 for connecting to complementary snap mechanism 626 of resistive sensor elements 608. In the illustrated embodiment, snap-mechanism 622 comprises a female snap mechanism. In other embodiments, however, snap-mechanism 622 could comprise a male snap mechanism. As discussed above, snap-mechanism 622 may be electrically connected to a conductor in cable 624. Snap-mechanism 622 may be electrically insulated from metallization layer 676 by suitable etching of metallization layer 676 or some other suitable insulating technique.

ECG systems (e.g. systems 100, 200, 300, 400) according to particular embodiments may include mechanisms for reducing the effects of ambient electrical noise. More particular, ECG systems according to particular embodiments may comprise one or both of a grounding strap (not shown) or a right leg electrode (not shown). Such a grounding strap or right leg electrode may be used in addition to the grounding techniques implemented in electrode units 104 and/or in addition to filtering techniques provided by signal processing components described above to reduce the ambient electrical noise's impact on received electrical heart activity signals. Some sources of ambient noise (e.g. power line hum that could be either 60 Hz or 50 Hz) may be too strong to be effectively filtered by using the signal processing circuitry of the ECG systems. Accordingly, in some embodiments, one or both of a grounding strap or a right leg electrode may be used to increase the signal-to-noise ratio for subsequent signal processing.

A grounding strap may be provided to link the negative side of the power source (e.g. battery (not shown)) of base unit 102 to the patient's skin while limiting the current flow for patient safety. Such a grounding strap may be similar to the grounding straps used in electronics laboratories and/or electronic fabrication facilities and may be worn so as to touch the patient's skin to be effective for ambient electrical noise rejection (e.g. common mode rejection of the amplifiers associated with electrode units 104).

A Right Leg Drive (RLD) electrode may be implemented to inject the "inverted" polarity noise of same amplitude as an ambient electrical noise onto the patient's skin in order to compensate for the common mode noise. The RLD circuitry may comprise an inverting amplifier, a filter and a safety limiting resistor to prevent exceeding the safety limit of the noise signal injected onto the skin. This RLD electrode may or may not touch the skin in order to inject inverted ambient noise into the system. The DSP may use the inverted ambient noise signal from the RLD electrode to at least partially cancel ambient noise and to thereby increase the signal-to-noise ratio. A RLD electrode may be provided with similar physical characteristics as electrode unit 600 described above and may comprise a clamp portion similar to clamp portion 602 for attaching to a patient's clothing or the like.

In some embodiments, ECG systems 100, 200, 300, 400 (FIGS. 4A-4D) are portable and lightweight systems that are convenient to use and transport. For example, they may be compact enough to be carried by hand so that they are easy to transport to a patient's current location, which may be in the patient's home or in some other location. In some embodiments, ECG systems 100, 200, 300, 400 may be designed to be small enough to fit within a carrying bag or pocket.

While a number of exemplary aspects and embodiments have been discussed above, those of skill in the art will recognize certain modifications, permutations, additions and sub-combinations thereof. For example:

In the illustrated embodiment of FIGS. 6A and 6B, cable 624 is shown as being permanently attached to sensor portion 604. This is not necessary. In some embodiments, cable 624 may be attached to clamp portion 602 and the outputs of sensor portion 604 (e.g. sensed signals) may be connected to cable 624 by suitable electrical contact(s) between clamp portions 602 and sensor portion 604. In some embodiments, connections to resistive sensor elements (e.g. snap mechanism 622 and/or clamp contacts 636) can be routed through clamp portion 602 without the need for sensor portion 602.

In some embodiments, clamp portion 602 of electrode unit 600 may be fabricated from bacteria resistant material (e.g. suitable plastic and/or the like).

In some embodiments, ECG systems 100, 200, 300, 400 may be configured to provide a heart-shaped graphic on display 120 and to interpret the ECG data to cause the heart-shaped graphic to simulate actual heart-muscle activity as detected in the ECG data.

In some embodiments, multi-mode electrode units 600 (or any variations of multi-mode electrodes 600 described herein) may be connected to prior art ECG systems—e.g. in the place of conventional electrode units. When connected in this manner, suitable adapters may be used to provide output signals from electrode units 600 in a format useable by the prior art ECG system.

In some embodiments, cables (e.g. cables 106, cables 624) associated with the various electrode units described herein may be retractable and may be housed, for example, in the base unit or in the housing of the electrode unit.

In some embodiments, an electrode unit comprising a capacitive sensor element 606 (see FIGS. 6A, 6B) could be incorporated into a blood pressure cuff and attached to the body of a patient via the blood pressure cuff to sense heart muscle electrical activity in a field-sensing contact or field-sensing non-contact mode.

It is therefore intended that the scope of the following appended claims and claims hereafter introduced should not be limited by the embodiments set forth in the examples, but should be given the broadest interpretation consistent with the description as a whole.

What is claimed is:

1. A system for monitoring heart muscle activity of an individual comprising:
   a first electrode unit for generating a first signal indicative of electrical activity of the heart muscle at a first location on a body of the individual; and
   a second electrode unit for generating a second signal indicative of electrical activity of the heart muscle at a second location on the body of the individual;
   wherein each of the first and second electrode units is configurable to operate in:
     a field-sensing mode wherein the electrode unit is configured to generate its corresponding signal based on a detected electric field at a location on or in proximity to the individual's skin; and,
     a current-sensing mode wherein the electrode unit is configured to generate its corresponding signal based on current flow through a resistive sensor element placed directly on the individual's skin;
   wherein each of the first and second electrode units is configurable to operate in:
     a non-contact field-sensing mode wherein the individual's clothing is located between the electrode unit and the individual's skin; and
     a contact field-sensing mode wherein the individual's clothing is not located between the electrode unit and the individual's skin
   wherein each of the electrode units comprises a capacitive sensor element, the capacitive sensor element of each of the electrode units comprising:
     an electrodynamic sensor which is sensitive to electromagnetic waves; and
     an antenna comprising an electrically conductive radiating element for receiving electromagnetic waves, the radiating element in electrical contact with a sensing surface of the electrodynamic sensor and having a surface area which is larger than a surface area of the sensing surface of the electrodynamic sensor, the antenna located relatively more proximate than the electrodynamic sensor to the individual's skin during operation of the electrode unit in the field-sensing mode.

2. The system according to claim 1 wherein:
   the first electrode unit is configured to operate in the field-sensing mode to thereby generate the first signal based on the detected electric field at the location on or in proximity to the individual's skin;
   the second electrode unit is configured to operate in the current-sensing mode to thereby generate the second signal based on current flow through the resistive sensor element placed directly on the individual's skin; and
   wherein the system is configured to combine the first signal and the second signal to generate an ECG waveform.

3. The system according to claim 1 wherein the capacitive sensor element of each of the electrode units comprises an electrically non-conductive layer disposed on the radiating element, wherein the non-conductive layer is on an outside face of the electrode unit which is located relatively more proximate than the radiating element to the individual's skin during operation of the electrode unit in the field-sensing mode.

4. The system according to claim 1 wherein at least one of the electrode units comprises a clamp.

5. The system according to claim 4 wherein the clamp is provided in a clamp portion of the electrode unit, the capacitive sensor element is provided in a sensor portion of the electrode unit and the clamp portion and sensor portion are attachable to, and detachable from, one another.

6. The system according to claim 4 wherein the clamp comprises a pair of clamp teeth for clamping objects therebetween and the clamp is shaped to clamp the individual's clothing between the clamp teeth and to thereby affix the at least one electrode unit to the individual's clothing when operating in the non-contact field-sensing mode.

7. The system according to claim 4 wherein the clamp comprises a pair of clamp teeth for clamping objects therebetween and one or more electrically conducting clamp contacts located in one or both of the teeth for clamping an electrically conductive tab on the resistive sensor element between the clamp teeth and corresponding electrical attachment of the resistive sensor element to the one or more clamp contacts.

8. The system according to claim 1 wherein at least one of electrode units comprises a first connector component for receiving a second complementary connector component of the resistive sensor element for removably electrically connecting the resistive sensor element to the electrode unit by connecting the first and second connector components.

9. The system according to claim 8 wherein the first and second connector components are shaped such that connecting the first and second connector components causes deformation of at least one of the first and second connector components and corresponding restorative forces which tend to maintain the connection between the first and second connector components.

10. The system according to claim 1 wherein the capacitive sensor element of each electrode unit comprises a first connector component for receiving a second complementary connector component of the resistive sensor element for removably electrically connecting the resistive sensor element to the electrode unit by connecting the first and second connector components, the first connector component located on a side of the electrodynamic sensor opposite that of the antenna.

11. A system for monitoring heart muscle activity of an individual comprising:
a first electrode unit for generating a first signal indicative of electrical activity of the heart muscle at a first location on a body of the individual; and
a second electrode unit for generating a second signal indicative of electrical activity of the heart muscle at a second location on the body of the individual;
wherein each of the first and second electrode units is configurable to operate in:
a field-sensing mode wherein the electrode unit is configured to generate its corresponding signal based on a detected electric field at a location on or in proximity to the individual's skin; and,
a current-sensing mode wherein the electrode unit is configured to generate its corresponding signal based on current flow through a resistive sensor element placed directly on the individual's skin;
wherein each of the first and second electrode units is configurable to operate in:
a non-contact field-sensing mode wherein the individual's clothing is located between the electrode unit and the individual's skin; and
a contact field-sensing mode wherein the dividual's clothing is not located between the electrode unit and the inddvidual's skin
wherein each of the electrode units comprises a capacitive sensor element, the capacitive sensor element of each of the electrode units comprising:
an electrodynamic sensor which is sensitive to electromagnetic waves; and
an antenna comprising an electrically conductive radiating element for receiving electromagnetic waves, the radiating element in electrical contact with a sensing surface of the electrodynamic sensor and having a surface area which is larger than a surface area of the sensing surface of the electrodynamic sensor, the antenna located relatively more proximate than the electrodynamic sensor to the individual's skin during operation of the electrode unit in the field-sensing mode; and
at least one of the electrode units comprises a first proximity sensor configured to detect a presence of the resistive sensor element.

12. The system according to claim 11 wherein the at least one of the electrode units comprises a second proximity sensor configured to detect proximity of the individual's skin and to thereby permit determination of whether the electrode unit is operating in the non-contact field-sensing mode or the contact field-sensing mode.

13. The system according to claim 1 wherein the first electrode unit is operating in the non-contact field-sensing mode simultaneously with the second electrode unit operating in the contact field-sensing mode and wherein the system is configured to combine the first signal and the second signal to generate an ECG waveform.

14. The system according to claim 1 wherein the first electrode unit is operating in the field-sensing mode simultaneously with the second electrode unit operating in the current-sensing mode and wherein the system is configured to combine the first signal and the second signal to generate an ECG waveform.

15. The system according to claim 1 comprising a base unit connected to the electrode units to receive the first and second signals, the base unit comprising a digital signal processor configured to generate one or more ECG waveforms based on a combination of the first and second signals.

16. The system according to claim 15 wherein at least one of the electrode units is integral with the base unit.

17. The system according to claim 15 wherein at least one of the electrode units is removably connected to the base unit by a corresponding cable.

18. The system according to claim 15 wherein at least one of the electrode units is wirelessly connected to the base unit.

19. The system according to claim 15 wherein the base unit is configured to display the one or more ECG waveforms on a display.

20. The system according to claim 19 wherein the display is removably connected to the base unit and the base unit and the display are configured for wireless communication of the one or more ECG waveforms from the base unit to the display when the display is removed from the base unit.

21. The system according to claim 15 comprising a grounding strap electrically connected to a power supply of the base unit, wherein, in operation, the grounding strap is placed directly on the individual's skin.

22. The system according to claim 15 wherein the digital signal processor is configured to process the first and second signals and to differentiate between portions of the signals attributable to heart muscle activity and portions of the signals attributable to one or more of the individual's breathing and the individual's body motion.

23. The system according to claim 15 wherein the digital signal processor is configured to scale at least one of the first and second signals to accommodate for differences in the strength of the signals due to operation of the first and second electrode units in different modes.

24. The system according to claim 23 wherein the digital signal processor is configured to automatically scale at least one of the first and second signals by automatic adjustment of amplifier gain of one or more amplifiers.

25. The system according to claim 1 comprising a right leg drive electrode configured to generate an inverted ambient noise signal and wherein the system is configured to use the inverted ambient noise signal to at least partially cancel ambient noise from the first and second signals.

26. A system for monitoring heart muscle activity of as individual comprising:
a first electrode unit for generating a first signal indicative of electrical activity of the heart muscle at a first location on a body of the individual, the first electrode unit comprising a first capacitive sensing element for detecting electric field;
a second electrode unit for generating a second signal indicative of electrical activity of the heart muscle at a second location on the body of the individual, the second electrode unit comprising a second capacitive sensing element for detecting electric field; and
a plurality of inputs, each input adapted to receive a corresponding signal from a current-sensing electrode unit indicative of electrical activity at a corresponding location on the body of the individual;
wherein the capacitive sensor element of each of the first and second electrode units comprises:

an electrodynamic sensor which is sensitive to electromagnetic waves; and an antenna comprising an electrically conductive radiating element for receiving electromagnetic waves, the radiating element in electrical contact with a sensing surface of the electrodynamic sensor and having a surface area which is larger than a surface area of the sensing surface of the electrodynamic sensor, the antenna located relatively more proximate than the electrodynamic sensor to the individual's skin during operation of the electrode unit.

27. The system according to claim 26 comprising:

a base unit configured to receive any available signals generated by the first and second electrode units and received at the plurality of inputs and to generate one or more ECG waveforms based on the available signals; and a display removably connected to the base unit;

the base unit and the display configured for wireless communication of the one or more ECG waveforms from the base unit to the display when the display is removed from the base unit.

28. The system according to claim 27 wherein the first and second electrode units are integrally housed in the base unit.

29. The system according to claim 27 wherein the plurality of inputs are provided on the base unit.

30. A system for monitoring heart muscle activity of an individual comprising:

a first input for receiving a first signal indicative of electrical activity of the heart muscle at a first location on a body of the individual;

a second input for receiving a second signal indicative of electrical activity of the heart muscle at a second location on the body of the individual;

a first field-sensing electrode unit connectable to the first input; and a second field-sensing electrode unit connectable to the second input;

wherein each of the inputs is adapted to receive a signal from a field-sensing electrode unit or from a current-sensing electrode unit and the system is configured to differentiate between signals received from field-sensing electrode units and signals received from current-sensing electrode units and to generate one or more ECG waveforms based on the received signals; and wherein each one of the first and second field-sensing electrode units comprises a capacitive sensor element, the capacitive sensor element comprising:

an electrodynamic sensor sensitive to electromagnetic waves;

an antenna comprising an electrically conductive radiating element for receiving electromagnetic waves, the radiating element in electrical contact with a sensing surface of the electrodynamic sensor and having a surface area which is larger than a surface area of the sensing surface of the electrodynamic sensor, the antenna located relatively more proximate, than the electrodynamic sensor to the individual's skin during operation of the field-sensing electrode unit.

31. The system according to claim 30 comprising:

a base unit which houses the first and second inputs; and a display removably connected to the base unit;

the base unit and the display configured for wireless communication of the one or more ECG waveforms from the base unit to the display when the display is removed from the base unit.

32. The system according to claim 30 comprising: a first field-sensing electrode unit connectable to the first input; and a second current-sensing electrode unit connectable to the second input.

33. The system according to claim 30 wherein the first electrode unit is connectable to the first input by way of a first flexible arm.

34. The system according to claim 33 wherein the first flexible arm comprises memory plastic.

35. The system according to claim 30 wherein the capacitive sensor element of each of the first and second field-sensing electrode units comprises an electrically non-conductive layer disposed on the radiating element, wherein the non-conductive layer is on an outside face of the field-sensing electrode unit which is located relatively more proximate than the radiating element to the individual's skin during operation of the field-sensing electrode unit.

36. The system according to claim 30 comprising one or more additional inputs, wherein each one of the one or more additional inputs is adapted to receive a corresponding additional signal from a field-sensing electrode unit or a current-sensing electrode unit, the corresponding additional signal indicative of electrical activity of the heart muscle at a corresponding location on the body of the individual.

37. The system according to claim 31 wherein the base unit comprise one or more of: a clip for connecting the base unit to the individual's clothing, arm or leg; and a strap for connecting the base unit to the individual's clothing arm or leg.

38. The system according to claim 31 wherein the base unit comprises one or more clips for removably attaching the first and second field-sensing electrode units to the base unit.

39. The system according to claim 31 wherein the first field-sensing electrode unit is housed in the base unit at a first position and the second field-sensing electrode unit is housed in the base unit at a second position spaced apart from the first position by a distance at least half of a length of the base unit.

40. The system according to claim 31 comprising a grounding strap electrically connected to a power supply of the base unit, wherein, in operation, the grounding strap is placed directly on the individual's skin.

41. The system according to claim 31 wherein the base unit comprises a digital signal processor configured to generate the one or more ECG waveforms based on one or more combinations of the received signals.

42. The system according to claim 41 wherein the digital signal processor is configured to process the received signals and to differentiate between portions of the signals attributable to heart muscle activity and portions of the signals attributable to one or more of the individual's breathing and the individual's body motion.

43. A system according to claim 41 wherein the digital signal processor is configured to scale at least one of the received signals to accommodate for differences in the strength of signals received from field-sensing electrode units and signals received from current-sensing electrode units.

44. The system according to claim 43 wherein the digital signal processor is configured to automatically scale at least one of the received signals by automatic adjustment of amplifier gain of one or more amplifiers.

45. The system according to claim 30 comprising a right leg drive electrode configured to generate an inverted ambient noise signal and wherein the system is configured to use the inverted ambient noise signal to at least partially cancel ambient noise from the first and second signals.

46. The system for monitoring heart muscle activity of an individual comprising:
- a first field-sensing electrode unit for generating a first signal indicative of electrical activity of the heart muscle at a first location on a body of the individual, the first field-sensing electrode unit configured to generate the first signal based on a detected electric field at a location on or in proximity to the individual's skin; and
- a second current-sensing electrode unit for generating a second signal indicative of electrical activity of the heart muscle at a second location on the body of the individual, the second current-sensing electrode unit configured to generate the second signal based on current flow through a resistive sensor element placed directly on the individual's skin;
- wherein the system is configured to combine the first signal and the second signal to generate an ECG waveform; and
- the first field-sensing electrode unit comprises a capacitive sensor element, the capacitive sensor element comprising:
  - an electrodynamic sensor which is sensitive to electromagnetic waves; and
  - an antenna comprising an electrically conductive radiating element for receiving electromagnetic waves, the radiating element in electrical contact with a sensing surface of the electrodynamic sensor and having a surface area which is larger than a surface area of the sensing surface of the electrodynamic sensor, the antenna located relatively more proximate than the electrodynamic sensor to the invdidual's skin during operation of the first field-sensing electrode unit.

47. A system for monitoring heart muscle activity of an individual comprising:
- a first electrode unit for generating a first signal indicative of electrical activity of the heart muscle at a first location on a body of the individual; and
- a second electrode unit for generating a second signal indicative of electrical activity of the heart muscle at a second location on the body of the individual;
- wherein each of the first and second electrode units is configurable to operate in:
- a field-sensing mode wherein the electrode unit is configured to generate its corresponding signal based on a detected electric field at a location on or in proximity to the individual's skin; and,
- a current-sensing mode wherein the electrode unit is configured to generate its corresponding signal based on current flow through a resistive sensor element placed directly on the individual's skin; and
- wherein the first field-sensing electrode unit comprises a capacitive sensor element, the capacitive sensor element comprising:
  - an electrodynamic sensor which is sensitive to electromagnetic waves; and
  - an antenna comprising an electrically conductive radiating element for receiving electromagnetic waves, the radiating element in electrical contact with a sensing surface of the electrodynamic sensor and having a surface area which is larger than a surface area of the sensing surface of the electrodynamic sensor, the antenna located relatively more proximate than the electrodynamic sensor to the individual's skin during operation of the first field-sensing electrode unit.

48. A system for monitoring heart muscle activity of an individual comprising:
- a first electrode unit for generating a first signal indicative of electrical activity of the heart muscle at a first location on a body of the individual; and
- a second electrode unit for generating a second signal indicative of electrical activity of the heart muscle at a second location on the body of the individual;
- wherein each of the first and second electrode units is configurable to operate in a field-sensing mode wherein the electrode unit is configured to generate its corresponding signal based on a detected electric field at a location on or in proximity to the individual's skin; and
- wherein each of the electrode units comprises a capacitive sensor element, and the capacitive sensor element of each of the electrode units comprises:
  - an electrodynamic sensor which is sensitive to electromagnetic waves; and
  - an antenna comprising an electrically conductive radiating element for receiving electromagnetic waves, the radiating element in electrical contact with a sensing surface of the electrodynamic sensor and having a surface area which is larger than a surface area of the sensing surface of the electrodynamic sensor, the antenna located relatively more proximate than the electrodynamic sensor to the individual's skin during operation of the electrode unit in field-sensing mode.

* * * * *